(12) United States Patent  
Schiller et al.

(10) Patent No.: US 7,988,663 B2
(45) Date of Patent: Aug. 2, 2011

(54) RETRACTABLE NEEDLE SYRINGE ASSEMBLY

(75) Inventors: Eric R. Schiller, Kinnelon, NJ (US); Christina J. D'Arrigo, Hoboken, NJ (US); Douglas Paddock, Hardyston, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/573,650

(22) PCT Filed: Aug. 12, 2005

(86) PCT No.: PCT/US2005/028919
§ 371 (c)(1),
(2), (4) Date: Jun. 5, 2007

(87) PCT Pub. No.: WO2006/020953
PCT Pub. Date: Feb. 23, 2006

(65) Prior Publication Data
US 2008/0097308 A1   Apr. 24, 2008

(51) Int. Cl.
*A61M 5/00* (2006.01)
(52) U.S. Cl. .......................... 604/110; 604/198
(58) Field of Classification Search .................. 604/110, 604/198
See application file for complete search history.

(56) References Cited

U.S. PATENT DOCUMENTS

| | | |
|---|---|---|
| 4,375,815 A | 3/1983 | Burns |
| 4,388,925 A | 6/1983 | Burns |
| 4,449,529 A | 5/1984 | Burns |
| 4,527,561 A | 7/1985 | Burns |
| 4,535,769 A | 8/1985 | Burns |
| 4,553,541 A | 11/1985 | Burns |
| 4,616,649 A | 10/1986 | Burns |
| 4,624,253 A | 11/1986 | Burns |
| 4,677,979 A | 7/1987 | Burns |
| 5,431,672 A | 7/1995 | Cote et al. |
| 5,533,970 A * | 7/1996 | Berger et al. ................. 604/110 |
| 5,578,011 A | 11/1996 | Shaw |
| 5,632,733 A | 5/1997 | Shaw |
| 5,752,968 A | 5/1998 | Jolly et al. |
| 5,792,162 A | 8/1998 | Jolly et al. |
| 5,797,880 A | 8/1998 | Erskine |
| 5,830,190 A | 11/1998 | Howell |
| 5,919,201 A | 7/1999 | Carter et al. |
| 5,938,676 A | 8/1999 | Cohn et al. |
| 5,941,892 A | 8/1999 | Cohn et al. |
| 6,010,486 A | 1/2000 | Carter et al. |
| 6,036,674 A | 3/2000 | Caizza et al. |

(Continued)

FOREIGN PATENT DOCUMENTS

WO   WO/96/35463   11/1996

(Continued)

*Primary Examiner* — Nicholas D Lucchesi
*Assistant Examiner* — Gerald Landry, II
(74) *Attorney, Agent, or Firm* — Jeanne P. Lukasavage; Diehl Servilla LLC

(57) ABSTRACT

A syringe including a barrel (14), a retractable needle (12) and a plunger rod assembly (22) including inner (30) and outer (24) members with a stopper (46) for expelling fluids from the syringe is disclosed. An activation member (40, 44) associated with the plunger rod permits relative movement of the inner and outer members when activated. The stopper is configured to compress a sufficient amount when advanced distally in the barrel to cause the activation element to engage and cause retraction of the needle within the syringe.

22 Claims, 25 Drawing Sheets

U.S. PATENT DOCUMENTS

| | | | |
|---|---|---|---|
| 6,053,929 A | 4/2000 | Cohn et al. | |
| 6,086,568 A | 7/2000 | Caizza | |
| 6,090,077 A | 7/2000 | Shaw | |
| 6,177,037 B1 | 1/2001 | Mayer | |
| 6,183,440 B1 | 2/2001 | Bell | |
| 6,221,052 B1 | 4/2001 | Caizza et al. | |
| 6,368,303 B1 | 4/2002 | Caizza | |
| 6,409,701 B1 | 6/2002 | Cohn | |
| 6,413,237 B1 * | 7/2002 | Caizza et al. | 604/110 |
| 6,432,087 B1 | 8/2002 | Hoeck et al. | |
| 6,517,516 B1 | 2/2003 | Caizza | |
| 6,558,357 B1 | 5/2003 | Hoeck | |
| 6,585,690 B1 | 7/2003 | Hoeck et al. | |
| 6,599,268 B1 | 7/2003 | Townsend et al. | |
| 6,632,198 B2 | 10/2003 | Caizza | |
| 6,689,106 B2 | 2/2004 | Bush, Jr. et al. | |
| 6,776,776 B2 * | 8/2004 | Alchas et al. | 604/198 |
| 6,840,291 B2 | 1/2005 | Caizza | |
| 6,926,700 B2 | 8/2005 | Bressler et al. | |
| 6,932,803 B2 | 8/2005 | Newby | |
| 6,952,604 B2 | 10/2005 | DeNuzzio et al. | |
| 7,018,344 B2 | 3/2006 | Bressler et al. | |
| 7,083,599 B2 | 8/2006 | Alchas et al. | |
| 7,104,622 B2 * | 9/2006 | Fukano et al. | 347/9 |
| 7,108,675 B2 | 9/2006 | Deboer et al. | |
| 7,182,734 B2 | 2/2007 | Saulenas et al. | |
| 7,258,678 B2 | 8/2007 | Wilkinson et al. | |
| 7,294,118 B2 | 11/2007 | Saulenas et al. | |
| 7,344,517 B2 | 3/2008 | Schiller | |
| 7,351,224 B1 | 4/2008 | Shaw | |
| 7,426,408 B2 | 9/2008 | DeNuzzio et al. | |
| 7,597,684 B2 | 10/2009 | Alchas et al. | |
| 7,604,613 B2 | 10/2009 | Crawford et al. | |
| 7,713,245 B2 | 5/2010 | Cipoletti et al. | |
| 2003/0045838 A1 * | 3/2003 | Woodard et al. | 604/218 |
| 2003/0125676 A1 | 7/2003 | Swenson et al. | |
| 2003/0125677 A1 | 7/2003 | Swenson et al. | |
| 2003/0163096 A1 | 8/2003 | Swenson et al. | |
| 2003/0181867 A1 | 9/2003 | Bressler et al. | |
| 2004/0102737 A1 * | 5/2004 | Wu | 604/218 |
| 2005/0215951 A1 * | 9/2005 | Saulenas et al. | 604/110 |
| 2006/0129173 A1 | 6/2006 | Wilkinson | |
| 2007/0129675 A1 | 6/2007 | Summerville et al. | |
| 2007/0260193 A1 | 11/2007 | Chin et al. | |
| 2008/0097344 A1 | 4/2008 | McKinnon et al. | |
| 2008/0243075 A1 | 10/2008 | Shaw | |

FOREIGN PATENT DOCUMENTS

| | | |
|---|---|---|
| WO | WO/98/48869 | 11/1998 |
| WO | WO-03/090815 | 11/2003 |

* cited by examiner

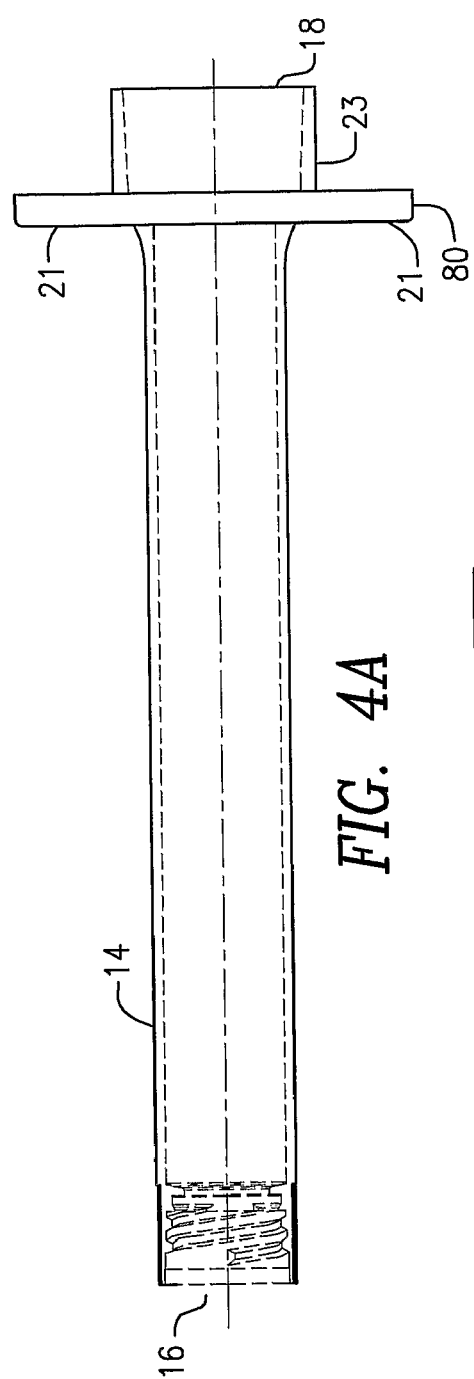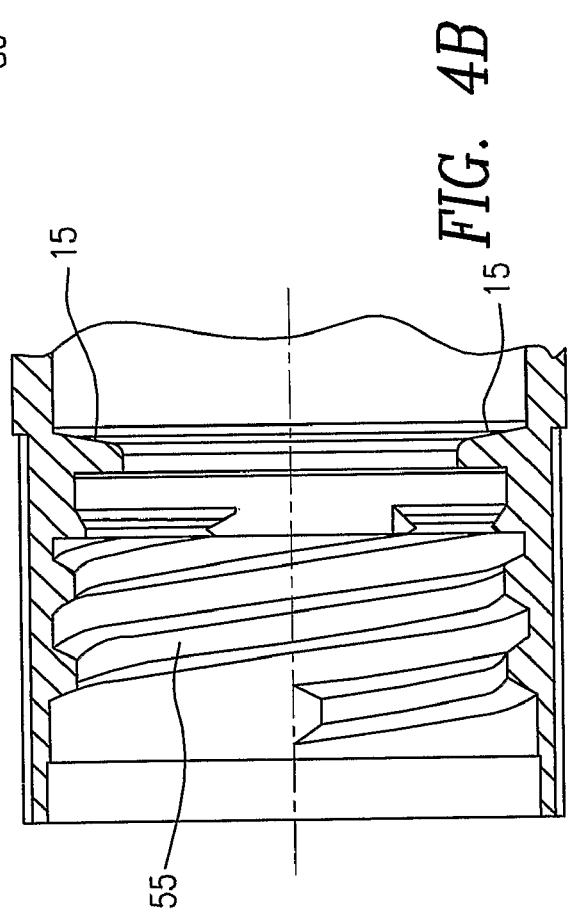

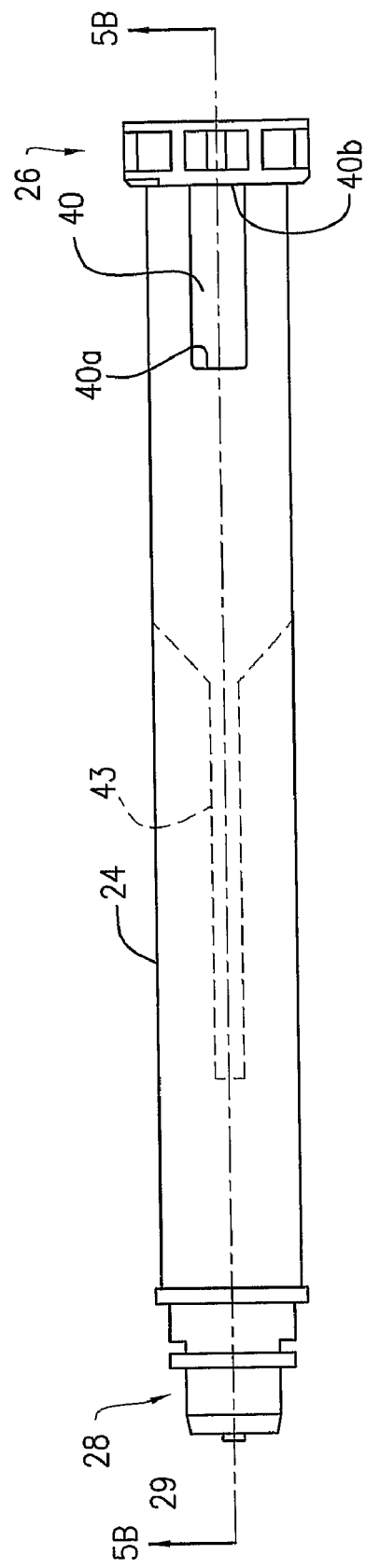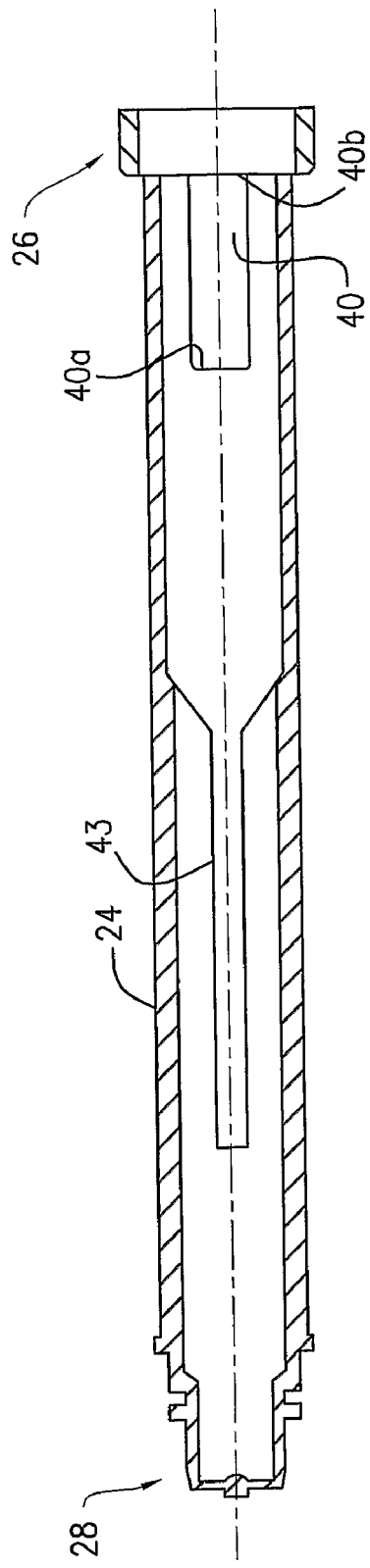
FIG. 5A
FIG. 5B

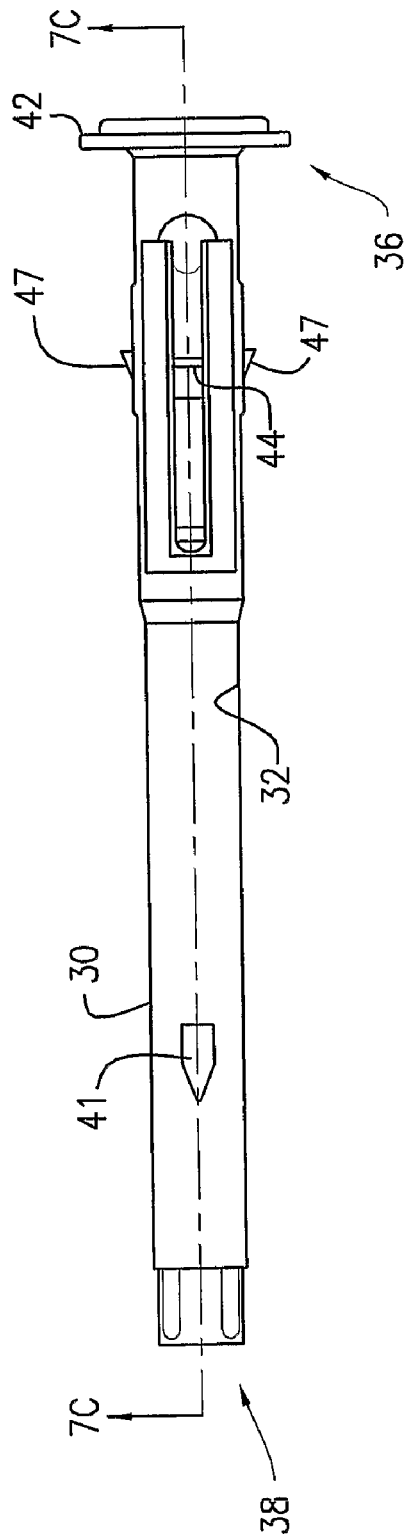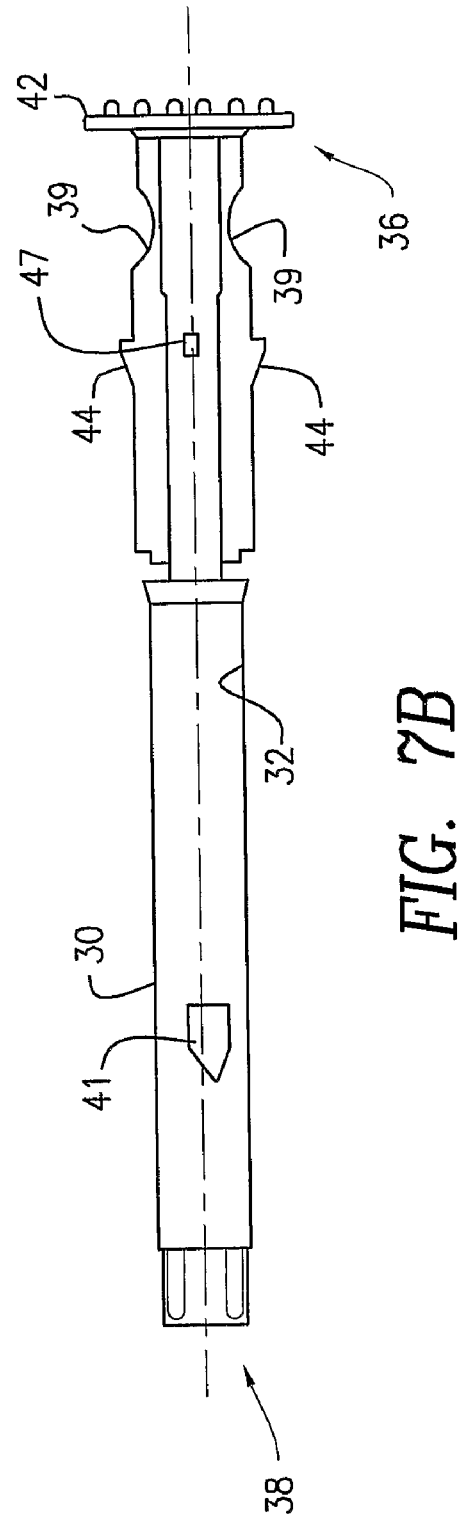
FIG. 7A
FIG. 7B

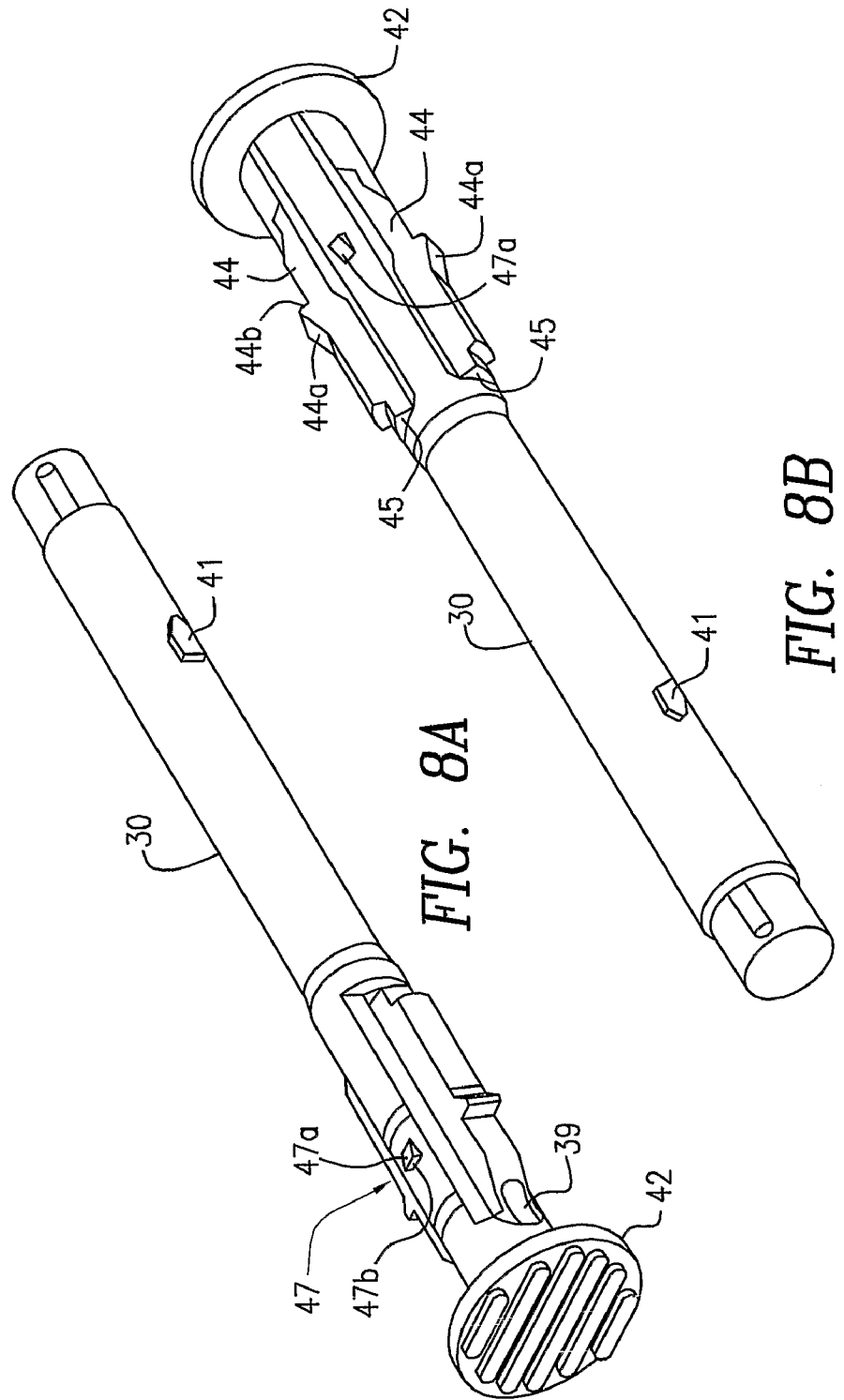

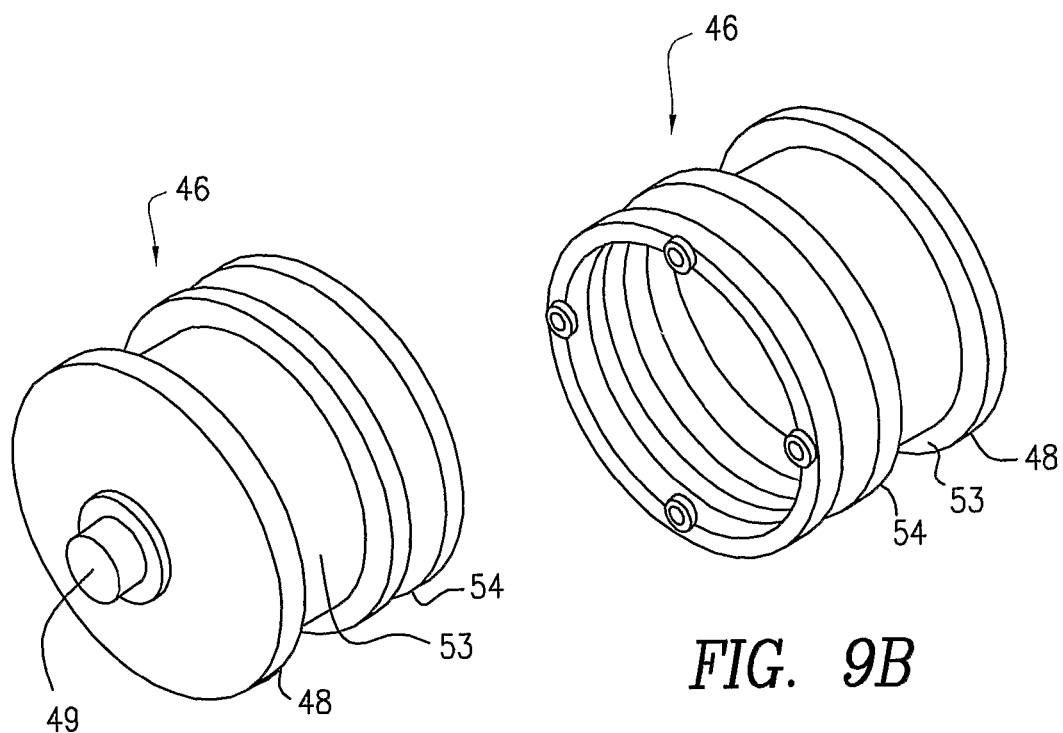
FIG. 9A
FIG. 9B
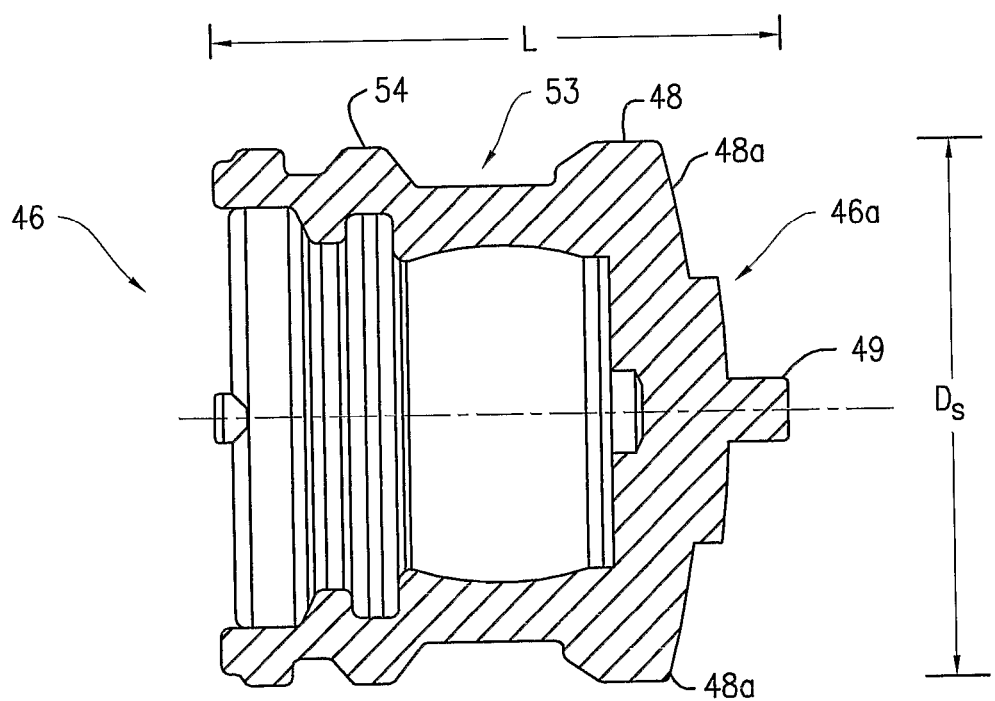
FIG. 9C

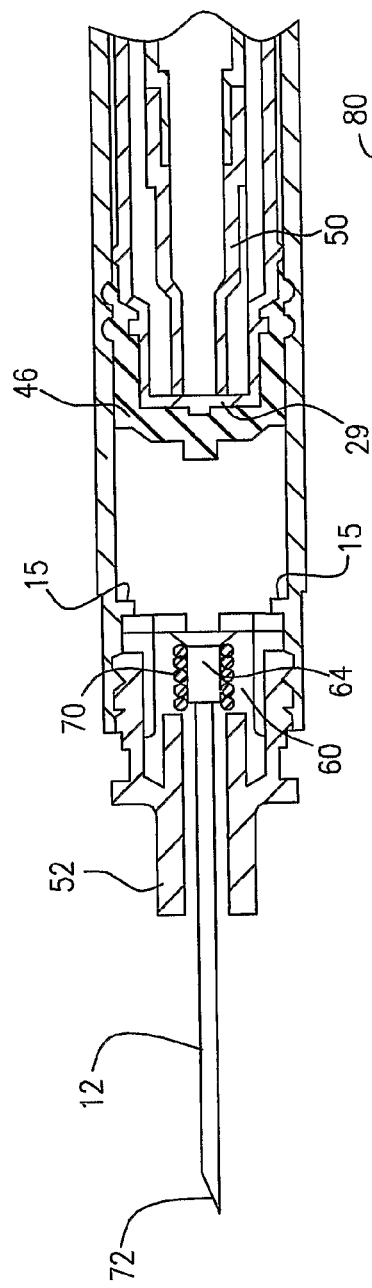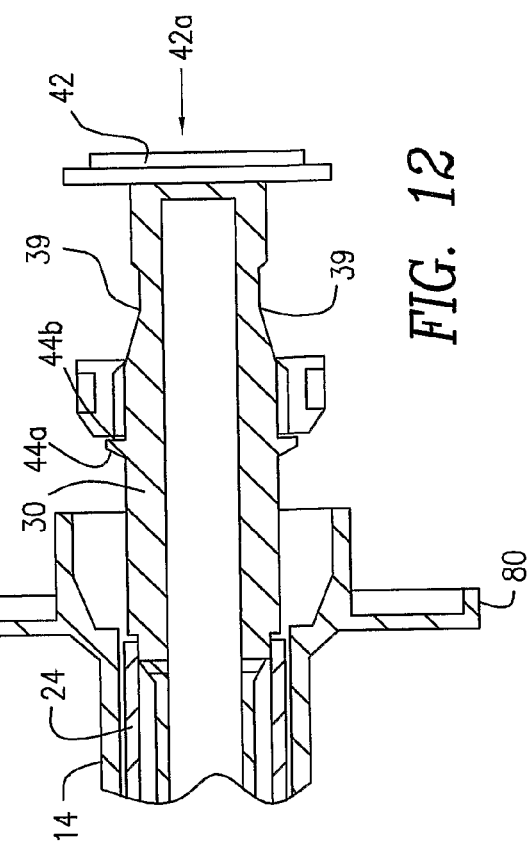

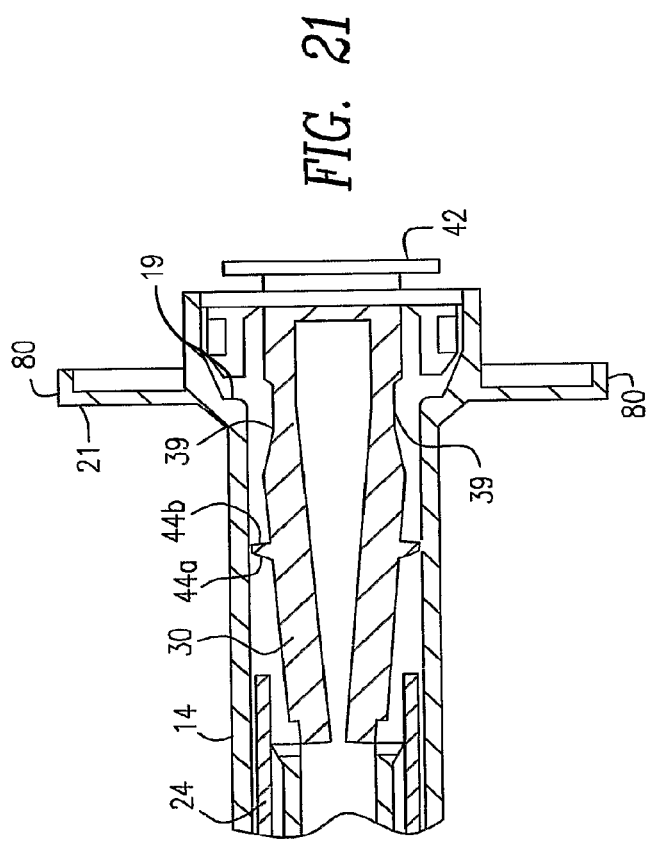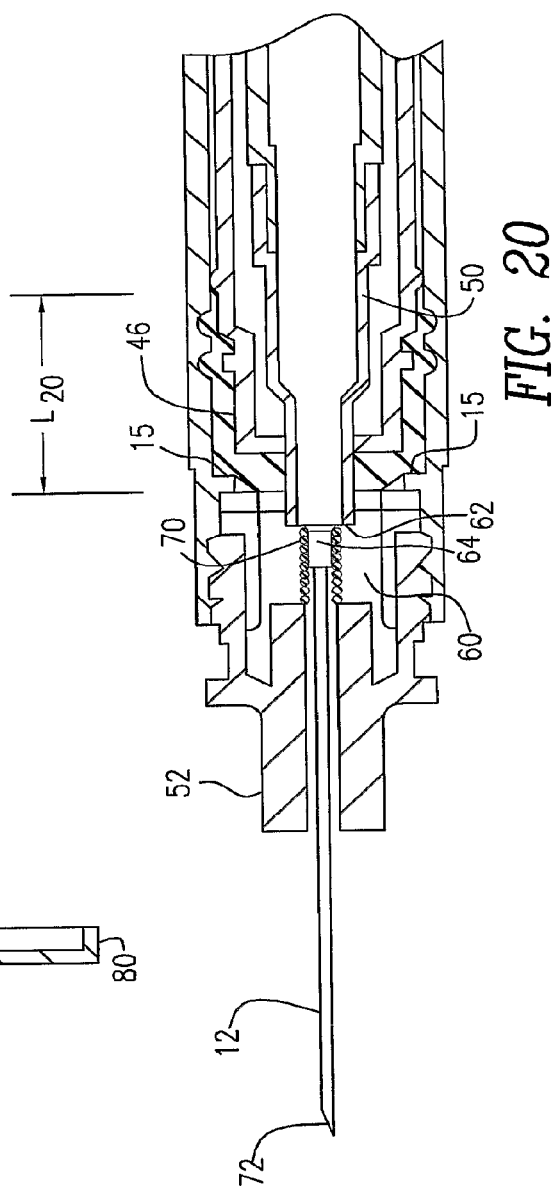

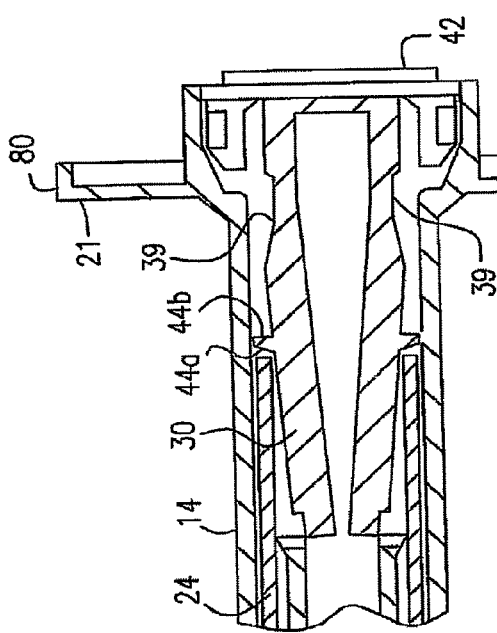
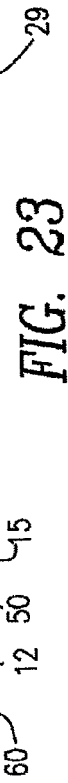
FIG. 24
FIG. 23

RETRACTABLE NEEDLE SYRINGE ASSEMBLY

TECHNICAL FIELD

Embodiments of the present invention generally relate to syringes and needle assemblies. Specific embodiments of the invention more particularly relate to syringe assemblies that include a needle that is retractable after the intended use to substantially prevent inadvertent exposure to the needle and reuse of the syringe and methods for manufacturing needle assemblies.

BACKGROUND ART

Hypodermic syringes are widely used in the medical arts for administering medicaments and for drawing body fluid samples. Generally, hypodermic syringes include a fixedly or removably attached metal needle that has a sharpened distal point for penetrating vial stoppers or a patient's skin. Hypodermic syringes and needles have been used for many years with few problems reported, taking into consideration the vast numbers and needles used. More recently, with the recognition of viral diseases that are transmitted by body fluids and greater sensitivity of the need to protect health care workers from inadvertent contact with previously used needles (commonly referred to as "sharps") as well as the need to reduce misuse of improperly disposed of needles and syringes, syringes and needles that include provisions to prevent reuse have been developed.

Provisions intended to protect health care workers from accidental needle sticks and prevent reuse of needles and syringes include a variety of sharps collector systems that are widely used in health care facilities. Other developments include needle attachments that may be readily broken off by practitioners once the syringe has completed its intended use. A variety of shielding mechanisms have been developed which are intended to shield the needle or sharp after it has been used, thus reducing the risk of an accidental needle stick. While many of these developments have reduced the incidence of inadvertent exposure of healthcare workers to sharps, most of these devices can readily be overcome by an individual determined to obtain and misuse a hypodermic syringe and needle. As a result of this problem, further developments in the art of hypodermic syringes have resulted in syringes with needles that withdraw into the body of the syringe once their intended use is completed. These are often referred to as retracting needle syringes.

Current conventional (i.e., non-retracting needle) syringes are considered by users to be virtually fault-free and reliable. They are used for a variety of different procedures involving both "one-shot" fill and inject procedures, as well as more complex mixing measuring and delivery functions. For retractable syringes to replace these functional, utilitarian and reliable conventional syringes, retractable syringes should not significantly interfere with the users current practices and they should be substantially reliable. In addition, in view of the fact that current conventional syringes are often manufactured at rates of several hundred per minute and their cost is generally not a significant factor in their usage, retractable syringes must be cost-effective to manufacture.

Most of the available retracting needle devices are somewhat complex, and many require manufacture and assembly of parts with potentially difficult assembly or tight tolerance requirements. Many of the designs depend upon a careful application of forces by the practitioner to draw and expel fluids from the syringe. Also, if the tolerances between the multiple components of the device are not carefully adhered to during manufacture and assembly, normal usage may result in premature activation of the retraction function of the syringe. The problem of premature activation of the retraction function is a problem with many available retracting needle syringes, particularly those that rely upon application of compressive force on the syringe stopper to activate the retraction mechanism. Many of the available retracting needle syringes have substantial undeliverable "dead volumes" that confound the practitioners need for accurate delivery of medicaments from the syringe or that may waste a substantial percentage of a high cost medicament that is left in the dead volume space. The problem of dead volumes may be associated with a syringe that relies on displacement of the plunger rod with respect to the syringe barrel. Previous syringe designs rely on either force against the stopper or displacement of the plunger rod to cause activation of the retraction mechanism.

Accordingly, a need exists for a selectively retractable syringe that can withstand normal forces during injection and avoid premature activation of the retraction mechanism. Moreover, there is a need to reduce the volume of waste space in the syringe and prevent leakage of medication from the syringe.

DISCLOSURE OF THE INVENTION

Embodiments of the invention pertain to a retractable syringe. In one embodiment, syringe including a retractable needle comprises a barrel having a fluid chamber defining a longitudinal axis and including a proximal end, and a distal end adapted to be attached to a needle; a plunger rod having a distal end and proximal end, the plunger rod including an inner sleeve slidably engageable within an outer housing. According to this embodiment, the inner and outer housing are axially moveable with respect to each other upon activation of a decoupling element associated with the plunger rod. The syringe of this embodiment further comprises compressible stopper mounted on the distal end of the of the plunger rod, the stopper being configured such that when distal force is applied to the plunger rod, the stopper is compressed in the direction of the longitudinal axis in an amount to allow distal movement of the plunger rod along the longitudinal axis a distance sufficient to permit activation of the decoupling element, causing the inner sleeve to move distally with respect to the outer housing and retraction of the needle within the syringe barrel.

In another embodiment, a syringe is provided which comprises a barrel having a fluid chamber, an inside surface, a proximal end, a proximal shoulder located on the inside surface, a distal end adapted to be attached to a needle and a ceiling located on the inside surface and adjacent the distal end. According to this embodiment, the syringe further comprises a plunger rod having a distal end and a proximal end, the plunger rod adapted to slidingly engage the inside surface of the fluid chamber, the plunger rod including a hollow outer housing defined by a wall and a hollow inner sleeve slidably receivable within the outer housing and defining a cavity, and a stopper located on the distal end of the plunger rod, the stopper including a distal face and an outer wall surface. The outer housing includes at least one window extending axially through the wall adjacent the proximal end of the plunger rod, and the inner sleeve includes at least one flexible finger adapted to be flexed inwardly towards the cavity, the flexible finger including a distal end, a proximal end, a distal facing ramp surface adapted to engage with the shoulder of the barrel and a distal facing edge. The inner sleeve further includes a proximal facing stop edge, the finger being sized and shaped to be received within the window, the stopper including a distal rib, a proximal rib and a gap region between the ribs located along the outer wall surface, wherein the configuration of the ramp surface and the stopper is such that axial compression of the stopper permits sufficient axial movement of the plunger rod so that ramp surface engages the shoulder of the barrel, causing inward deflection of the fingers and relative movement of the inner sleeve and outer housing and retraction of the needle.

In a further embodiment, a syringe including a retractable needle is provided, the syringe comprising a barrel including a distal end, a proximal end, an inner surface and an engagement surface; a plunger rod having a proximal end a distal end, the plunger rod adapted to be slidably received within the inner surface of the barrel, the plunger rod including an outer member and an inner member sized and configured to be slidably received within the inner member when an activation element is in contact with the engagement surface, the activation element including a flexible member associated with the inner member in contact with the outer member to prevent relative distal movement between the inner and outer members; and a stopper on the distal end of the plunger rod configured to permit axial movement sufficient to allow displacement of the plunger rod to permit the engagement element to contact the activation surface when the stopper is engaged against the distal end of the barrel.

BRIEF DESCRIPTION OF THE DRAWINGS

FIG. 4A is a side elevation view of a syringe barrel of FIG. 1;

FIG. 4B is in an enlarged side elevation view of the proximal portion of the barrel shown in FIG. 4A;

FIG. 5A is a side elevation view of the plunger outer housing shown in FIG. 1;

FIG. 5B is a cross-sectional view taken along line 5B-5B of FIG. 5A;

FIG. 7A is a side elevation of the plunger inner sleeve shown in FIG. 1;

FIG. 7B is a view of the plunger shown in FIG. 7A, rotated 180 degrees about the longitudinal axis of the plunger;

FIG. 8A is a proximal perspective view of the plunger inner sleeve shown in FIG. 1;

FIG. 8B is a distal perspective view of the plunger inner sleeve shown in FIG. 1;

FIG. 9A is a distal perspective view of the stopper shown in FIG. 1;

FIG. 9B is a proximal perspective view of the stopper shown in FIG. 1;

FIG. 9C is a cross-sectional view taken along line 9C-9C of FIG. 9A;

FIG. 11 is an enlarged view of the distal portion of FIG. 10;

FIG. 12 is an enlarged view of the proximal portion of FIG. 10;

FIG. 20 is an enlarged view of the distal portion of FIG. 19;

FIG. 21 is an enlarged view of the proximal portion of FIG. 19;

FIG. 23 is an enlarged view of the distal portion of FIG. 22; and

FIG. 24 is an enlarged view of the proximal portion of FIG. 22.

BEST MODE FOR CARRYING OUT THE INVENTION

Figure 1:
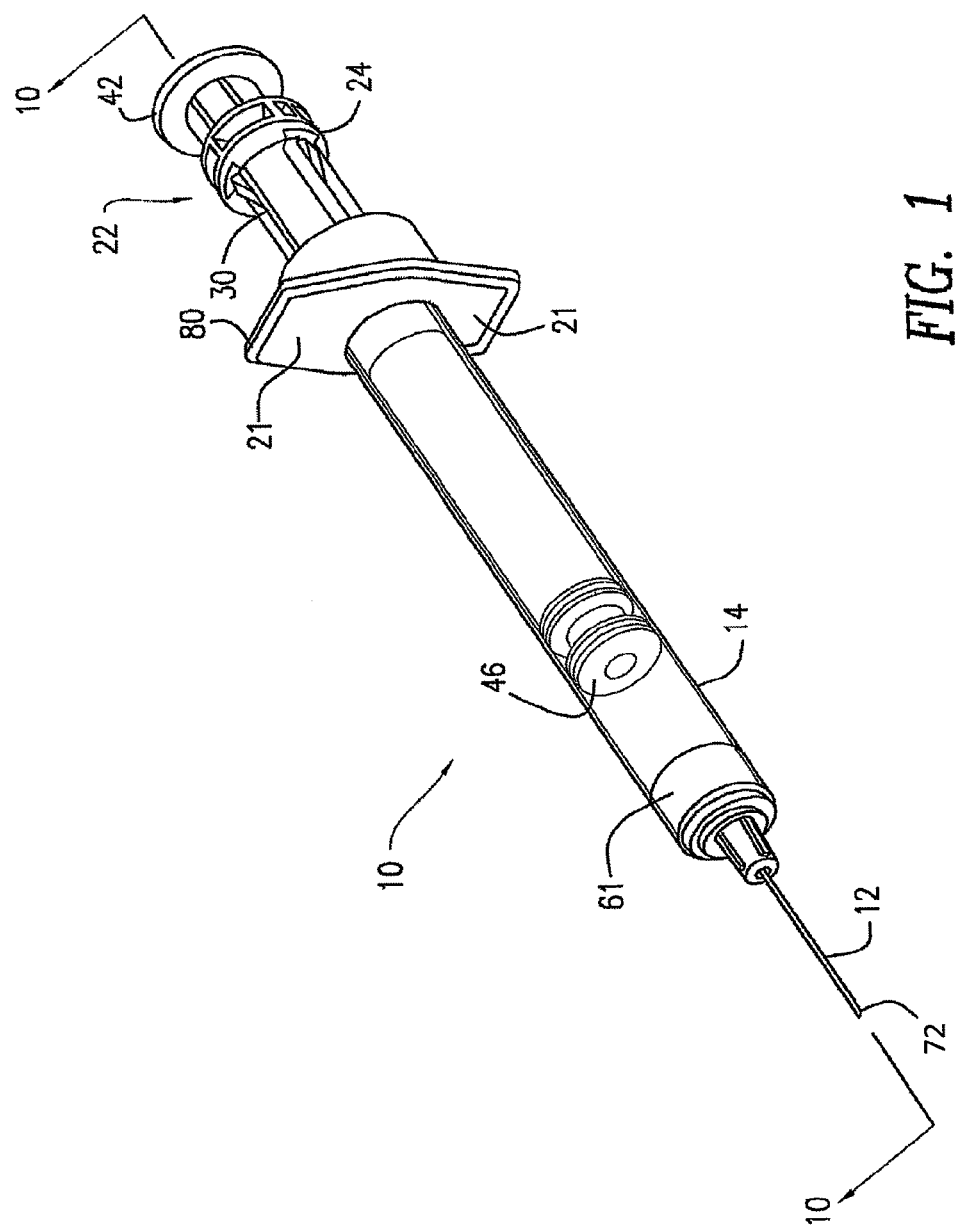
FIG. 1 is a perspective view of a hypodermic syringe according to an embodiment of the invention.

While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. The invention is capable of other embodiments and of being practiced or carried out in various ways.

In this disclosure, a convention is followed wherein the distal end of the device is the end closest to a patient and the proximal end of the device is the end away from the patient and closest to a practitioner.

Referring generally to FIGS. 1-24, an embodiment of a hypodermic syringe 10 with a selectively retractable needle 12 according to the present invention is shown. Referring first to FIGS. 1-4C, the syringe 10 includes an elongate barrel 14 having an open proximal end 16, an open distal end 18 and a hollow bore 20 therethrough. The proximal end of the barrel defines an internal shoulder 19, shown in FIG. 13. Finger flange 80 includes finger grips 21. Collar 23 is located on the exterior of the proximal end of the barrel 14. The distal end of the barrel defines a barrel roof or ceiling 15. As shown in the Figures, the barrel roof 15 surrounds the inner periphery of the barrel 14. The roof 15 retains a seal 17 on its distal side.

Figure 3:
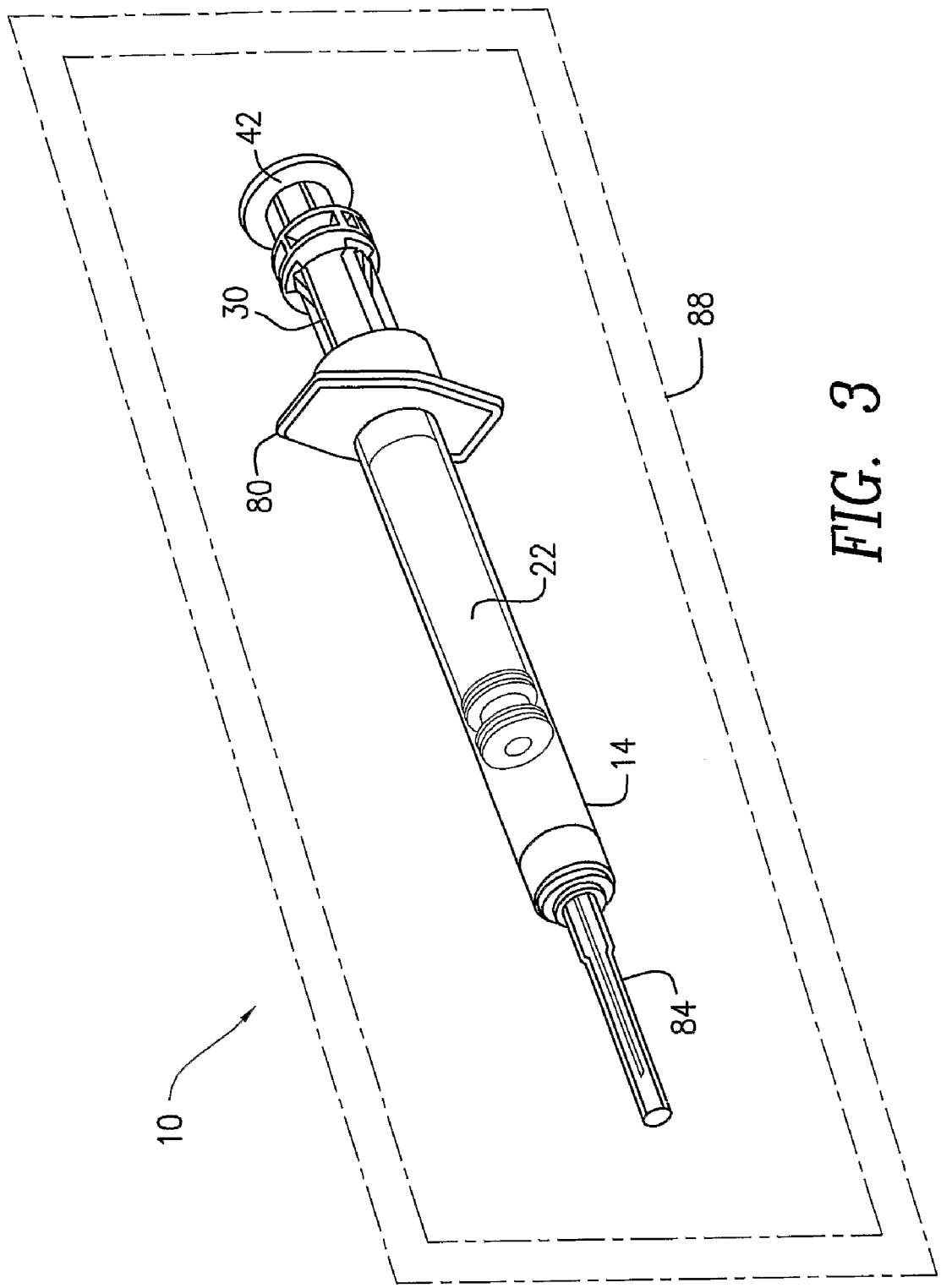
FIG. 3 is a perspective view of the syringe of FIG. 1 in a package.
Figure 4C:
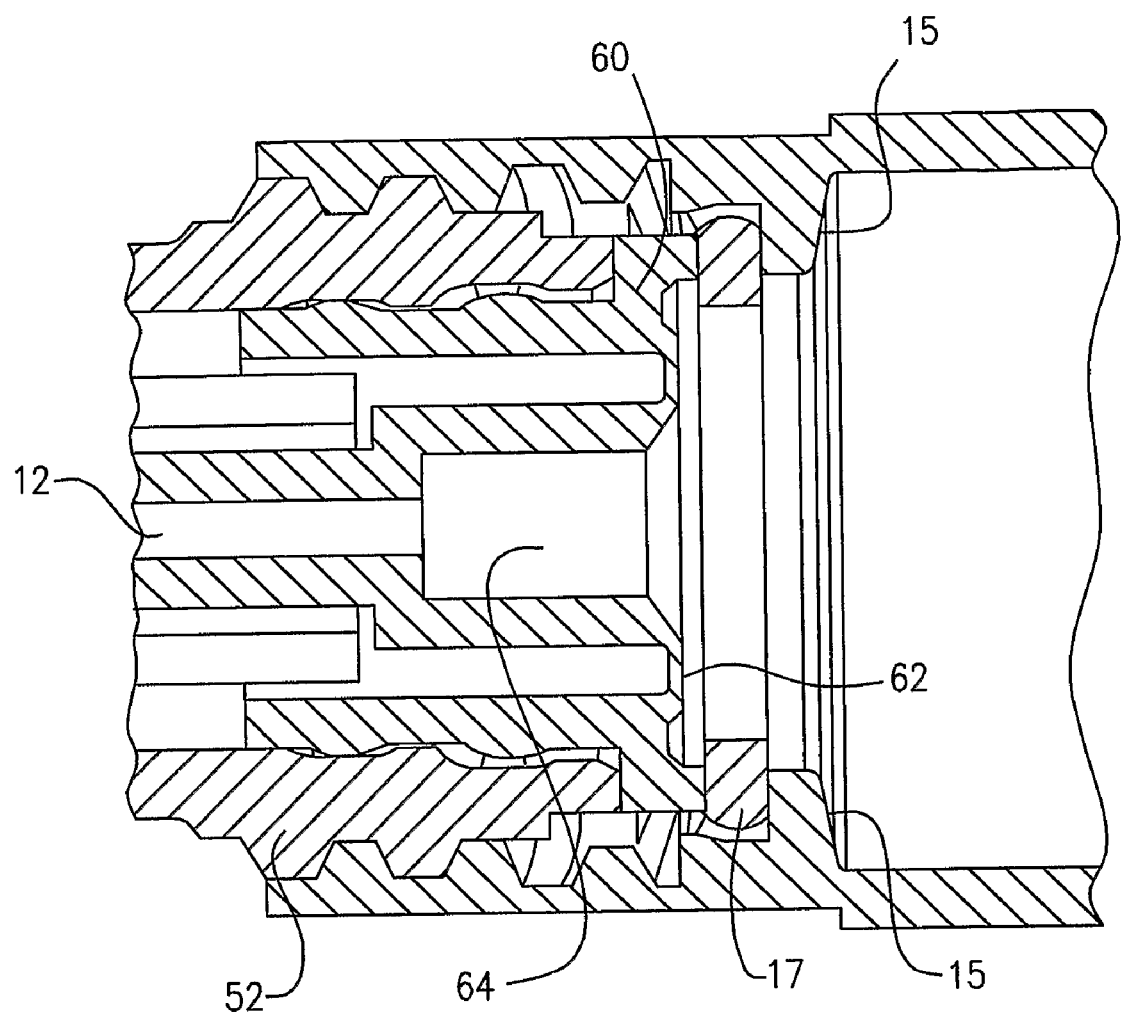
FIG. 4C is an enlarged side elevation view of the distal portion of the barrel attached to a needle and hub.
Figure 5C:
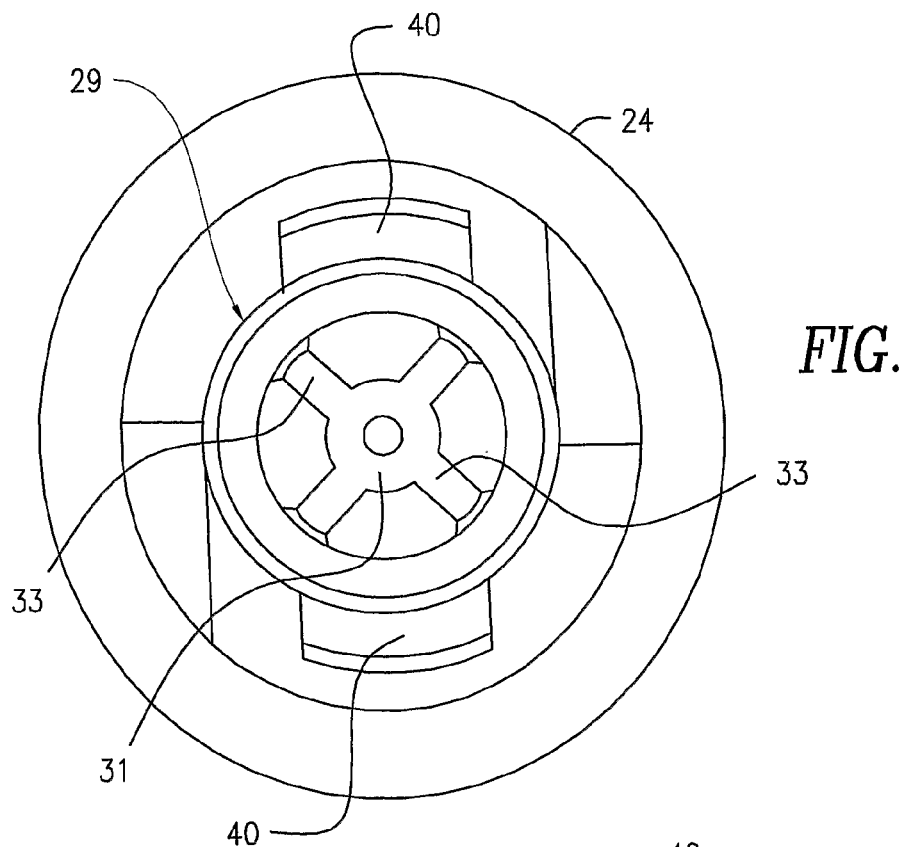
FIG. 5C is a distal end view of the plunger outer housing shown in FIG. 5A.
Figure 5D:
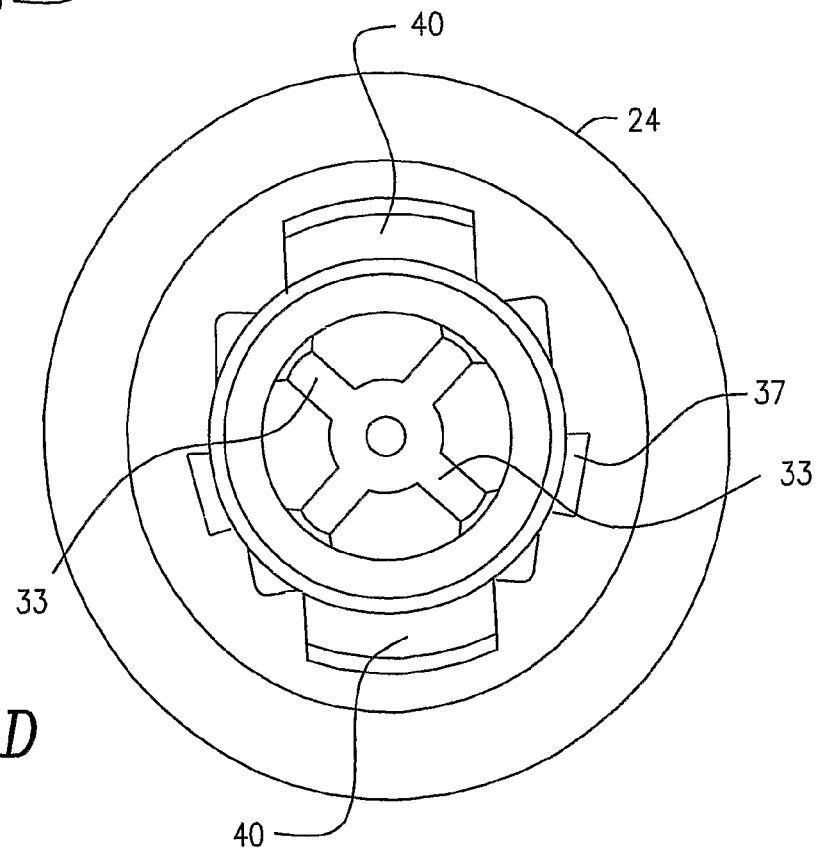
FIG. 5D is a proximal end view of the outer housing shown in FIG. 5A.
Figure 5E:
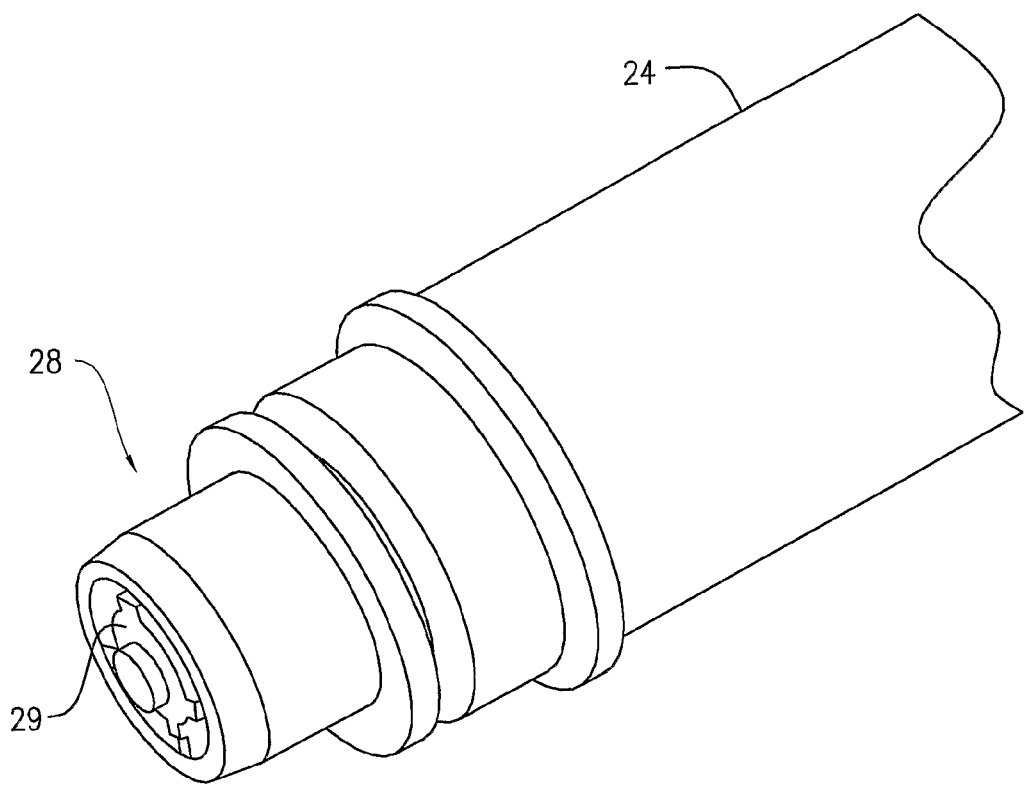
FIG. 5E is an enlarged perspective view of the distal portion of the outer housing shown in FIG. 5A.
Figure 6A:
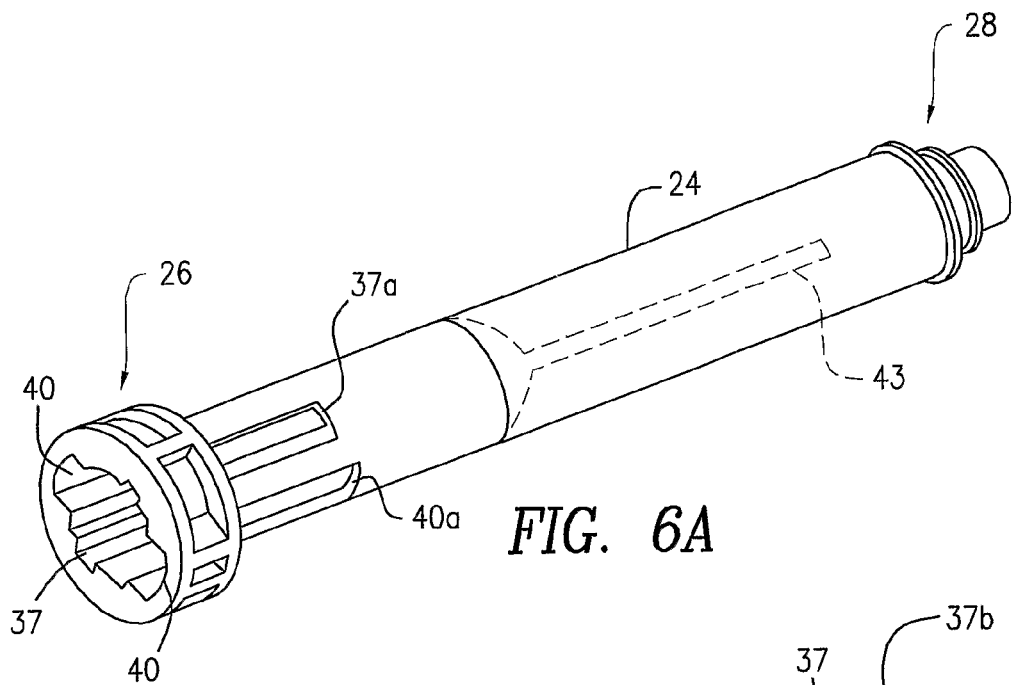
FIG. 6A is a proximal perspective view of the plunger outer housing shown in FIG. 1.
Figure 6B:
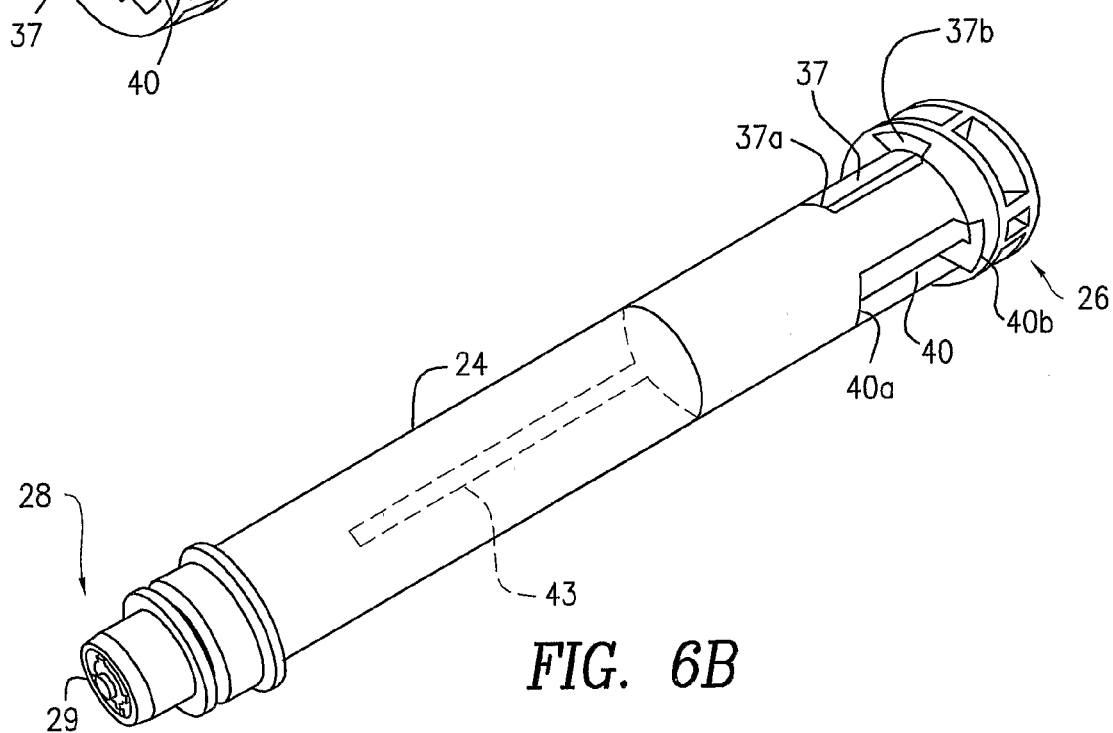
FIG. 6B is a distal perspective view of the plunger outer housing shown in FIG. 1.

Referring particularly to FIG. 3, syringe 10 is shown in FIG. 3 as being fitted with a needle shield 84 to protect sharp distal point 72 of needle 12 from damage prior to use. Syringe 10 is preferably sealed in a package 88 formed from materials substantially resistant to the passage of microorganisms and exposed to conditions that substantially render microorganisms therewithin substantially non-viable. Suitable materials for forming package 88 include, but are not limited to paper, non-wovens, polymeric film, metallic foil and combinations thereof. Suitable conditions for rendering microorganisms substantially non-viable include, but are not limited to, exposure to ionizing radiation, chemical sterilants and the like.

Referring now to FIGS. 1-8B, syringe 10 further includes an elongate plunger 22 sized to fit slidably within barrel 14 by advancing the plunger 22 into open proximal end 16 of barrel 14. As best seen in FIGS. 5A-8B, plunger 22 includes a hollow outer housing 24 and a hollow inner sleeve 30. Thus, the plunger 22 is comprised of the inner sleeve 30 and the outer housing 24. Referring to FIGS. 5A-6B, the outer housing 24 defines an open proximal end 26, a distal end 28 defining a webbing 29. Webbing 29 on the distal end 28 is shown as including a central hub 31 and spokes 33 radiating from the central hub 31. At least one window 40, and in the embodiment shown, two windows 40 are located adjacent proximal end 26. The windows 40 have a distal end 40a and a proximal end 40b and extend through the wall of the outer housing 24. At least one track 37 is located adjacent the windows 40, and the tracks have a distal end 37a and a proximal end 37b. The windows 40 and the tracks 37 extend partially along the axis of the outer sleeve and cooperate with features associated with the inner sleeve as described further below. In the embodiment shown, the windows 40 and the tracks 37 are shown as being elongate, the tracks 37 being narrower in width than the windows 40.

Referring now to FIGS. 7A-8B, the inner sleeve 30 defines a sidewall 32 which defines a cavity 34 therein with a proximal end 36 and an open distal end 38. A thumbpress 42 is located at the proximal end 38 of the inner sleeve 30. At least one, and in the embodiment shown, two fingers 44 are integrally formed in the inner sleeve and extend from the proximal end 36 towards the distal end 38. In the embodiment shown in FIGS. 7A-8B, the fingers 44 form a bending region 39 adjacent the proximal end 38 of the inner sleeve 30. The end opposite the bending region 39 of each finger 44 is a free end and includes a distal-facing edge 45. Distal-facing edge 45 is shown as being in the form of a stepped feature. The bending region 39 allows each finger 44 to flex inwardly towards cavity 34 by pressing inwardly on each finger 44. Fingers 44 also include ramps having a contact surface shown as a distal-facing ramp surface 44a, which is the portion of the finger 44 that is pressed upon during bending of the finger to inwardly bend the finger 44. The fingers also include a proximal-facing edge 44b. Proximal-facing edge 44b is shown as being at substantially a right angle to the longitudinal axis of the plunger. The inner sleeve 30 further includes lugs 47 located adjacent proximal end 36 of the plunger, including a distal-facing incline 47a and proximal-facing stop edge 47b.

Figure 2:
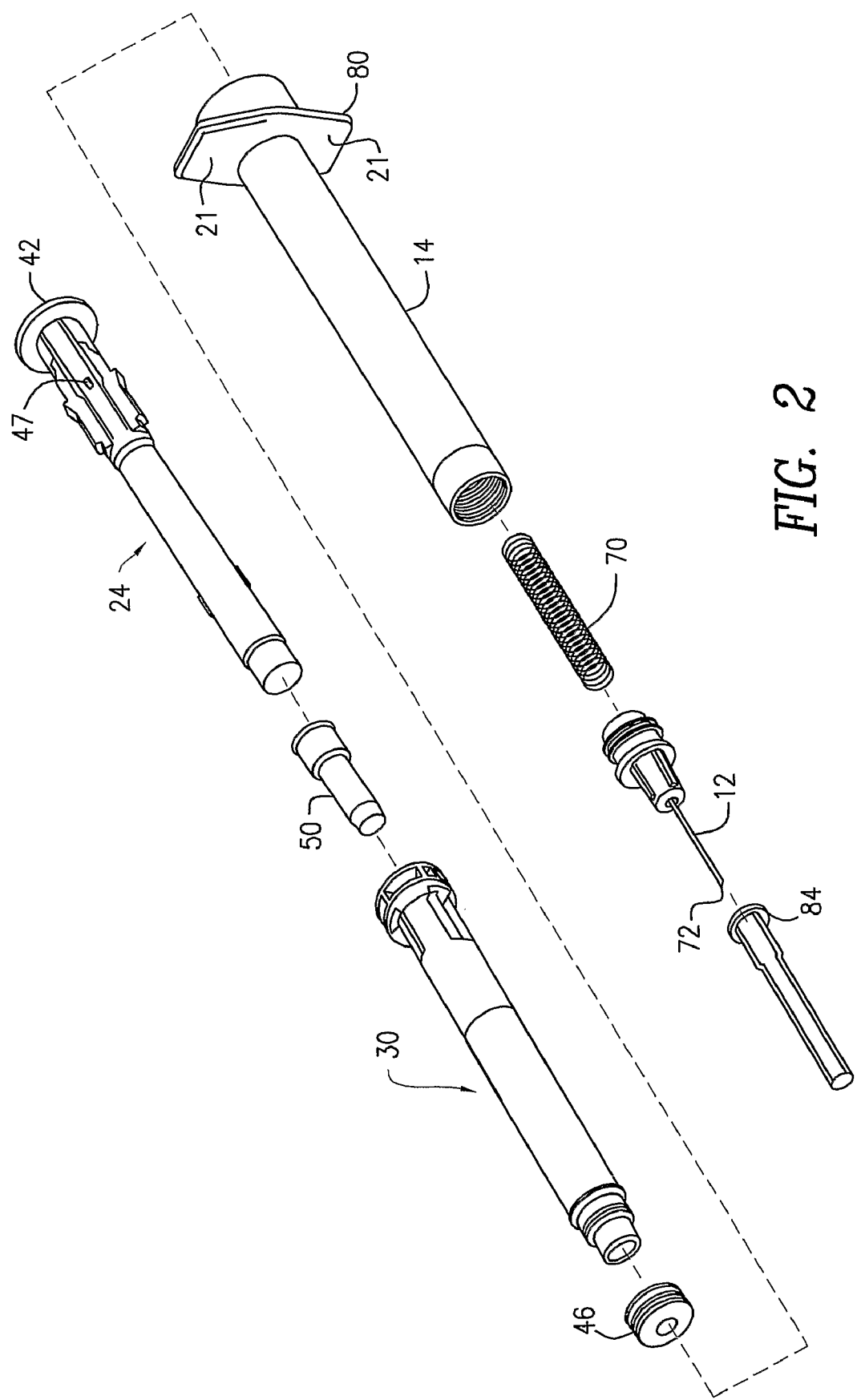
FIG. 2 is an exploded perspective view of the syringe of FIG. 1.

Inner sleeve 30 is radially sized to slidably fit within hollow outer housing 24 as shown in FIGS. 1 and 2 and described further below, and the fingers 44 of the inner sleeve 30 are sized and shaped to protrude through the windows 40 of the outer housing 24. In the embodiment shown, the fingers and the windows are shown as having a substantially rectangular shape and being located on radially opposite sides of the plunger, however, it will be understood that other shapes and configurations are within the scope of the invention. The lugs 47 are sized and shaped to protrude through the tracks 37 of the outer housing 24. The fingers 44 substantially prevent distal movement of inner sleeve 30 with respect to outer housing 24 in that the distal edges 45 of the fingers 44 contact distal edge 44a of each window to prevent the inner sleeve from moving distally with respect to the outer housing when distal force is applied to thumbpress 42 on the distal end of inner sleeve 24. Proximal facing stop edge 47b of lug 47 contacts proximal end 37b of track 37 to prevent the inner sleeve 30 from moving proximally with respect to outer housing 24 to prevent decoupling of the inner sleeve 30 from the outer housing 24 when proximal force is applied to the thumbpress 42 such as when the syringe is filled by drawing medicament into the barrel. It will be understood that instead of providing fingers 44 and separate lugs 47 and proximal facing stop edge 47b, the function of the lugs 47 and proximal facing stop edge 47b can be provided by proximal-facing edge 44b of finger 44 and proximal end 40b of window 40. Thus, in certain embodiments, the lugs 47 and tracks 37 can be eliminated, provided the finger 44 has sufficient stability to prevent bending of the finger 44 when proximal force is applied to the plunger rod during filling operation to prevent decoupling of the inner sleeve 30 and outer housing 24.

Figure 7C:
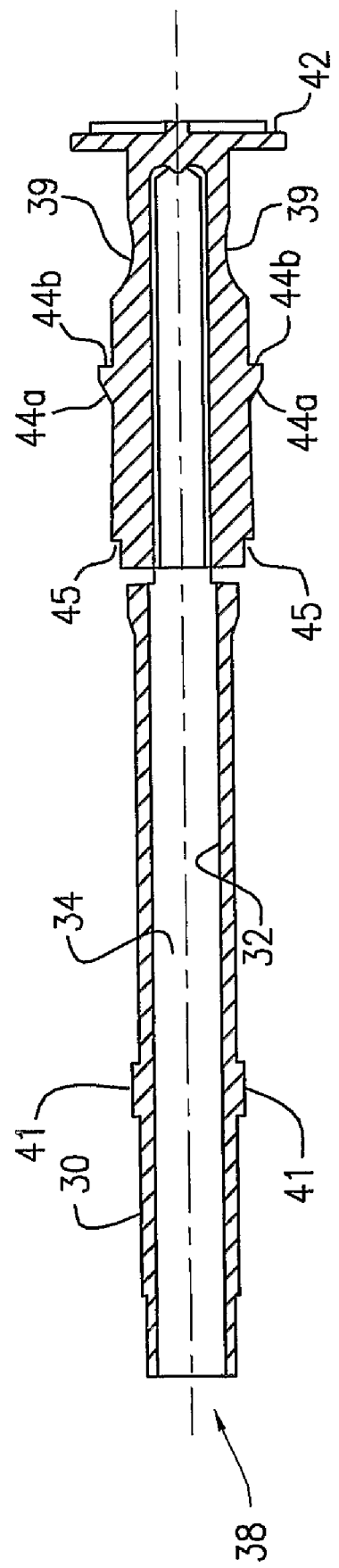
FIG. 7C is a cross-sectional view taken along line 7C-7C of FIG. 7A.

In certain embodiments, the plunger 22 further includes alignment features such as one or more bosses 41 located distally on inner sleeve 30 that cooperate with one or more optional alignment channels 43 located distally on the outer housing 24. The alignment channels 43 may fully extend through the wall of the outer housing 24, or, as shown in the Figures, they may form an elongate indentation on the inner surface of the outer housing 24. Referring to FIGS. 7A and 7B, FIG. 7A shows an elevation view of the inner sleeve 30, and boss 41 is substantially aligned with the center line shown as the dotted line in FIG. 7A. FIG. 7B is a view of the inner sleeve 30 rotated 180 degrees about its longitudinal axis and showing the other boss 41 as being slightly offset from the centerline. The alignment features 41, 43 ensure engagement and alignment between the inner sleeve 30 and the outer housing 24 during manufacturing and assembly of the plunger 22. Thus, as describe above with respect to FIGS. 7A and 7B, in one or more embodiments, one of the bosses 41 may be offset and the channels 43 may be helical in configuration to ensure the bosses do not hit point to point with the helical channels, which ensures that proper orientation of lugs 47 with respect to tracks 37 and fingers 44 with respect to windows 40. Stated another way, the bosses 41 may be asymmetrical with respect to one another, which ensures proper orientation. Thus, the bosses and channels are configured to guide the lugs 47 into alignment with the corresponding tracks 37 and the fingers 44 into alignment with their corresponding windows 40 of the outer housing 24. As shown in FIGS. 5A-5B and 6A-6B, the channels 43 are flared or funnel-shaped on their proximal end to ensure that the bosses 41 are guided into channels 43.

Referring now to FIGS. 9A-9C, plunger 22 further includes a stopper 46 mounted at distal end of the outer housing 24 for occluding the distal end that forms a slidable seal with hollow bore 20 of barrel 14 to define a chamber for drawing and expelling fluid from the syringe barrel. The stopper 46 has a diameter $D_s$ sized to form the slidable seal with the hollow bore 20 of the barrel 14. The stopper 46 includes distal face 46a and a projection 49 extending distally therefrom. When stopper 46 is mounted to distal end of plunger 22, webbing 29 of outer housing 24 supports distal face 46a during delivery of medication. Stopper 46 includes a distal rib 48 and proximal rib 54 spaced from each other to define gap region 53 on the outer wall surface of the stopper 46. The wall thickness of the stopper 46 is greater at the ribs 48, 54 than at in the gap region 53. The stopper has an overall axial length "L" that is at least about 50% of the diameter $D_s$ of the stopper. In certain embodiments, the axial length L of the stopper is at least about 75% of the diameter $D_s$ of the stopper, and in other embodiments, the axial length L of the stopper is equal to or greater than the diameter $D_s$ of the stopper.

The gap region has an axial length "$L_g$" that is at least about 30% of the diameter $D_s$ of stopper 46, and in certain embodiments, the axial length "$L_g$" of the gap region is at least about 40% of the diameter D. Rib 48 includes a distal contact surface 48a, which contacts roof 15 of barrel 14 when the plunger 22 is advanced distally and bottoms out at the distal end of the barrel 14. As best seen in FIG. 2 and further below, plunger 22 also includes a cutter 50 mounted at the distal end 38 of the inner sleeve disposed to cut through webbing 29 and stopper 46 to expose cavity 34 in the inner sleeve when the inner sleeve 30 is released from the outer housing, as will be described. Proximal side 15b of the roof 15 contacts only an outer peripheral portion 48 of the stopper distal face 46a, and in particular, distal contact surface 48a of rib 48 when the stopper 46 is advanced distally in the barrel 14.

Further components of the syringe 10, which are common in typical syringes, will now be described. Referring to FIGS. 10-24, syringe 10 includes a hub housing 52 and inner hub 60 defining that a proximal flange 62 and an axial stem 64, sized to fit within hub housing 52 with axial stem 64 extending distally. Flange 62 extends the roof 15 at the distal end of the chamber of the barrel. There is an elongate spring 70 disposed about stem 64 and compressed to provide a bias between flange 62 and hub housing 52. Syringe 10 further includes elongate hollow needle 12 extending from axial stem 64 in fluid communication with the barrel chamber. Flange 62 retains the needle 12 and stem 64 in position and prevents the needle 12 from retracting into barrel until the webbing 29 and flange 62 are cut as described further below.

Preferably, hub housing 52, hub 60 with needle 12 attached are formed into an assembly. Housing 52 preferably includes male threads (not shown) that cooperate with female threads 55 located at distal end 18 of barrel 14. This allows the releasable attachment of assembly 61 to barrel 14. While threads are preferred, other forms of attachment are known such as press-fit, snap fit and the like and are considered within the scope of the invention.

Seal 17 engages flange 62 of hub 60 thereby forming a substantially fluid tight seal between hub 60 and barrel 14. Thus, leakage is substantially reduced. The seal 17 is preferably made of thermoplastic elastomer, or other elastic material, such as rubber, TPE, silicone or similar property materials. The material is soft enough, Shore A hardness equal to ~55, to deform at low stresses from user applied torque, with a compression set of less than 25%. The seal may be assembled into the barrel during manufacturing. Alternatively, the seal may be molded to the needle hub.

Barrel 14 may be formed from thermoplastic materials such as polypropylene, polycarbonate, polyethylene and copolymers or any other suitable material used for the manufacture of syringe barrels. Plunger 22 is preferably formed from polypropylene, polyethylene, polystyrene and the like or any other suitable material used for the manufacture of syringe plungers. Cutter 50 is preferably formed form a metallic material such as stainless steel using a deep draw process or any other suitable forming process. Cutter 50 preferably is subjected to secondary processes such as electrochemical treatment, honing, sharpening, grinding and combinations of these processes to produce a sharpened surface at the distal end of cutter 50. The cutter 50 may also be made from plastic materials such as polycarbonate, polyetherketone, glass, ceramics, or mineral-filled polymers.

Figure 10:
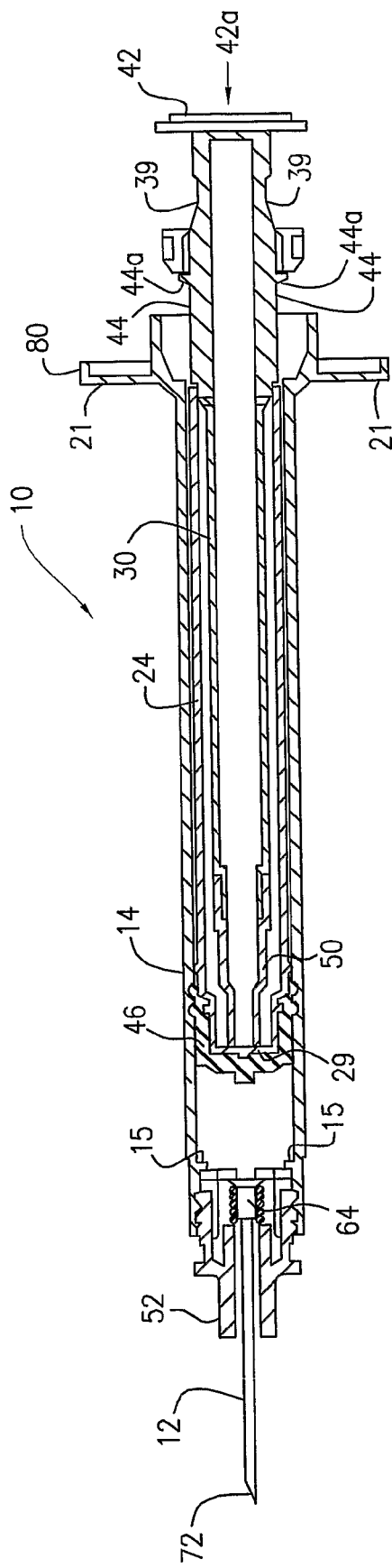
FIG. 10 is a cross-sectional view taken along line 10-10 of FIG. 1, showing the plunger located in a proximal position.

Referring still to FIGS. 10-24, the operation of the syringe will now be described. The syringe may be filled with medication by withdrawing the plunger rod by applying proximal force to the plunger rod 22 to fill the barrel chamber while the distal end of the syringe or needle 12 is immersed in medication. During filling, stop edge 47b of lugs 47 engage proximal ends 37b of tracks 37, preventing the inner sleeve 30 from decoupling from outer housing 24. After filling, a practitioner or user may then inject the medication by applying a distally directed force to the thumbpress 42 as shown by arrow 42a and holding fingers at finger grips 21 of finger flange 80. FIGS. 10-12 show the plunger 22 as it is being advanced distally in the barrel. Distal edge 45 of fingers 44 engage distal ends 40a of windows 40, causing the inner sleeve 30 and outer housing 24 to move in tandem distally within the barrel 14. During drug delivery, the full distal face 46a of stopper 46 is under pressure from medicament contained within the barrel of the syringe. Webbing 29 of outer housing 24 support distal face 46a during delivery of the medicament.

Figure 13:
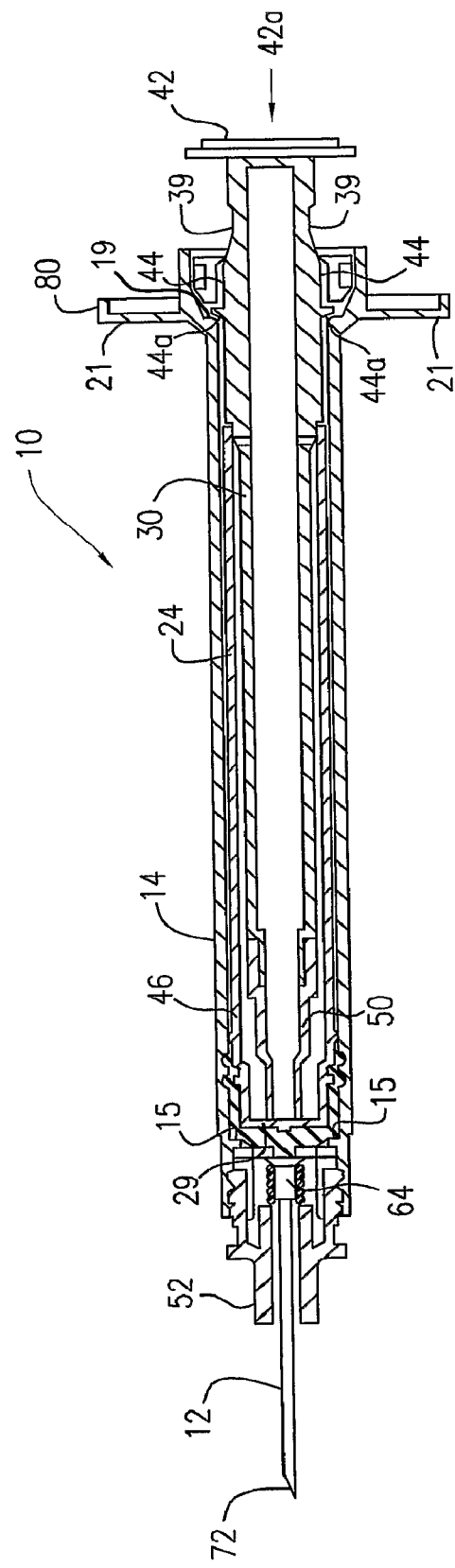
FIG. 13 is a cross sectional view of the syringe shown in FIG. 1, with the plunger advanced distally and the stopper advanced to the distal end of the barrel.
Figure 14:
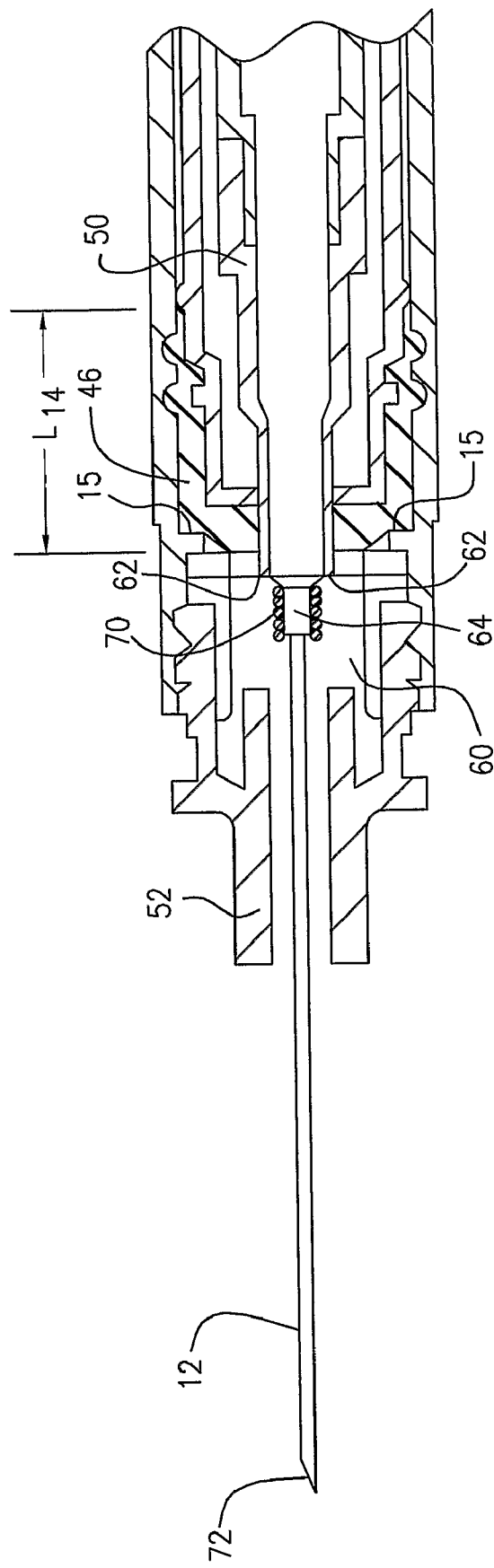
FIG. 14 is an enlarged view of the distal portion of FIG. 13.
Figure 15:
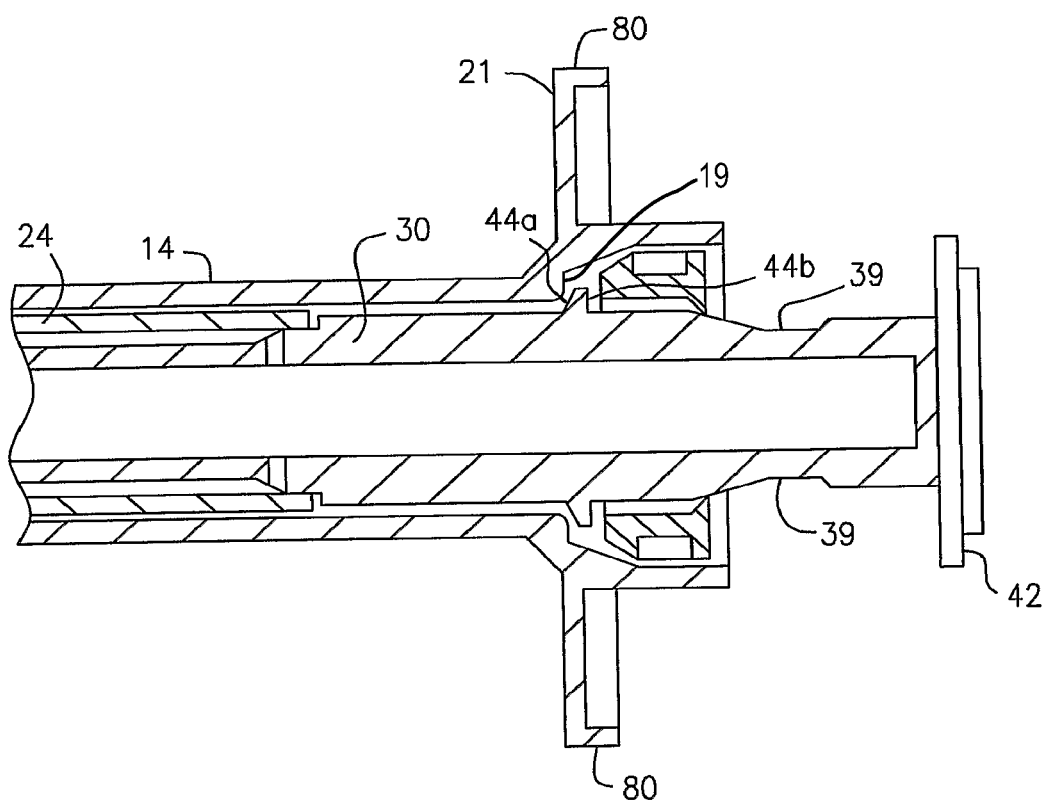
FIG. 15 is an enlarged view of the proximal portion of FIG. 13.
Figure 16:
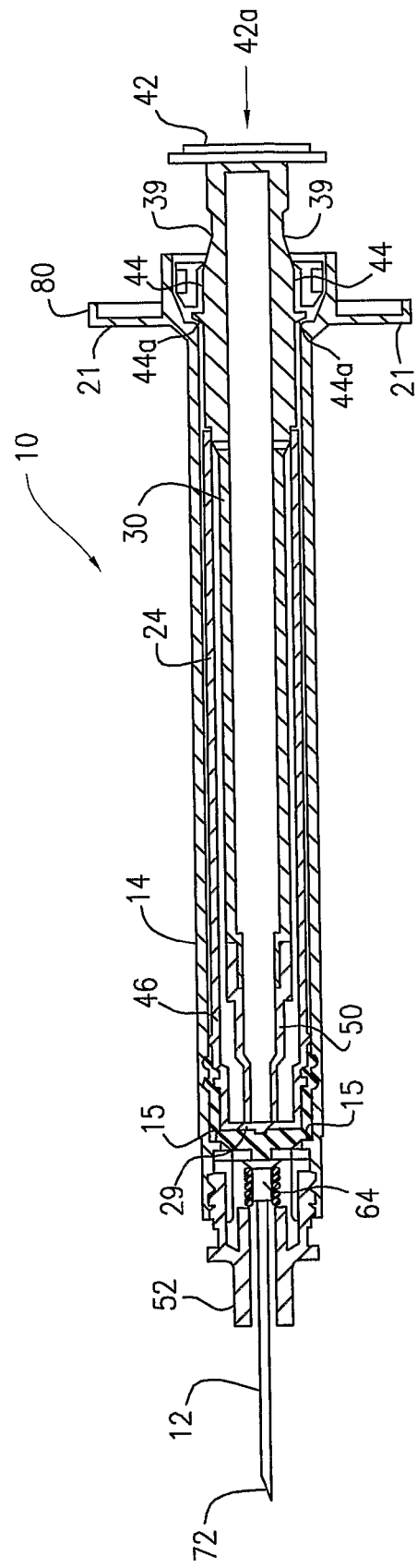
FIG. 16 is a cross-sectional view of the syringe shown in FIG. 1, with the plunger advanced distally further than shown in FIGS. 13-15 and the stopper partially compressed.
Figure 17:
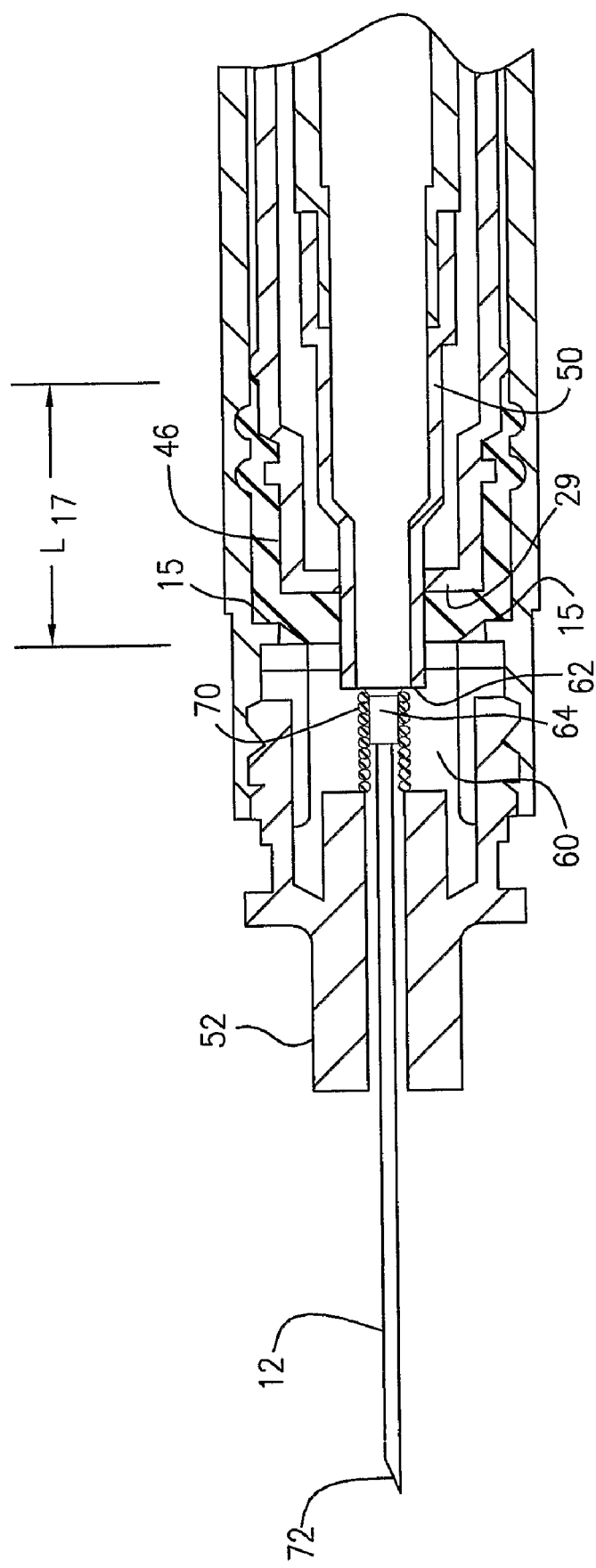
FIG. 17 is an enlarged view of the distal portion of FIG. 16.
Figure 18:
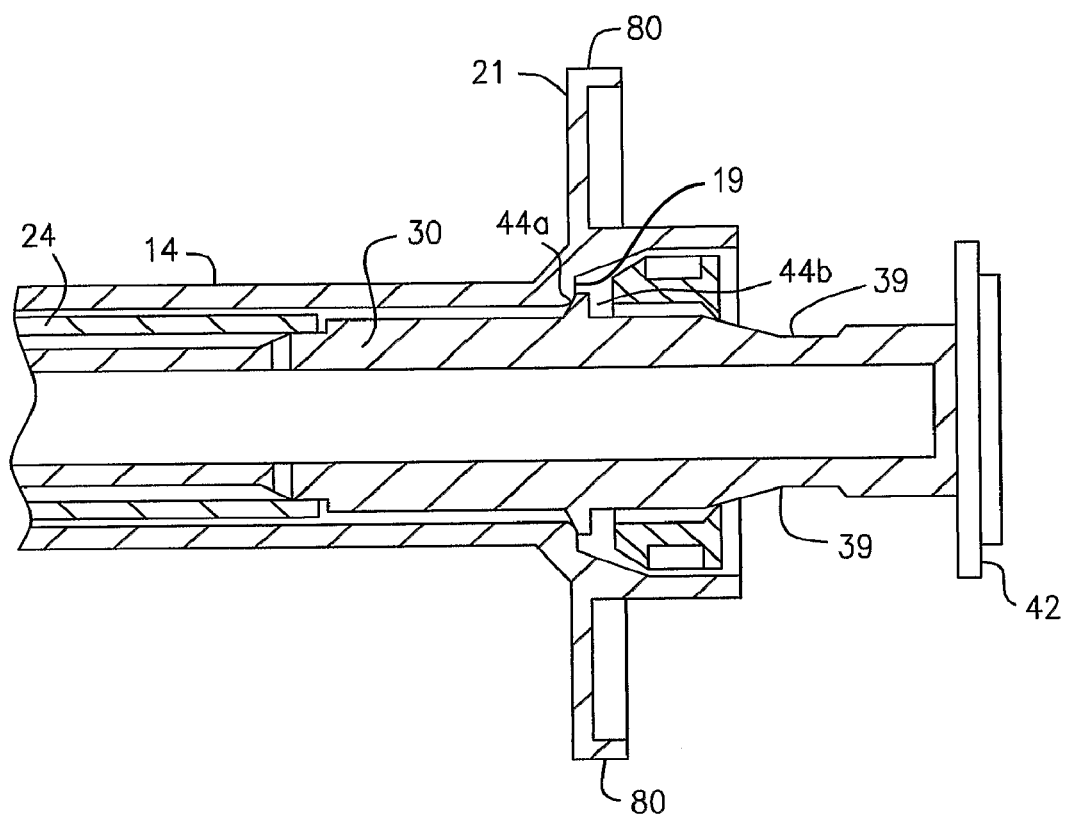
FIG. 18 is an enlarged view of the proximal portion of FIG. 16.

Referring now to FIGS. 13-15, syringe 10 is shown with the plunger 22 advanced distally in the barrel 14 at the completion of the delivery of the medication. The stopper 46 is bottomed out and distal contact surface 48a of rib 48 associated with the stopper is in contact with roof 15 of the barrel. The axial length of the stopper is indicated by "$L_{14}$". Ramp surfaces 44a of fingers 44 are positioned adjacent the shoulder 19 of barrel 14. Further distal force on the thumbpress 42 compresses the stopper, as shown in FIGS. 16-18. In FIGS. 16-18, the further distal force and movement of the plunger within the barrel 14, as the outer housing 24 and inner sleeve 30 are advanced together in tandem further distally until distal facing ramp surface 44a of the fingers 44 contact the shoulder 19 of barrel 14. The stopper 46 compresses further, causing the gap region 53 to decrease in size. The axial length of the stopper at this stage of compression is indicated as $L_{17}$, which is less than the length $L_{14}$ shown in FIG. 14.

Figure 19:
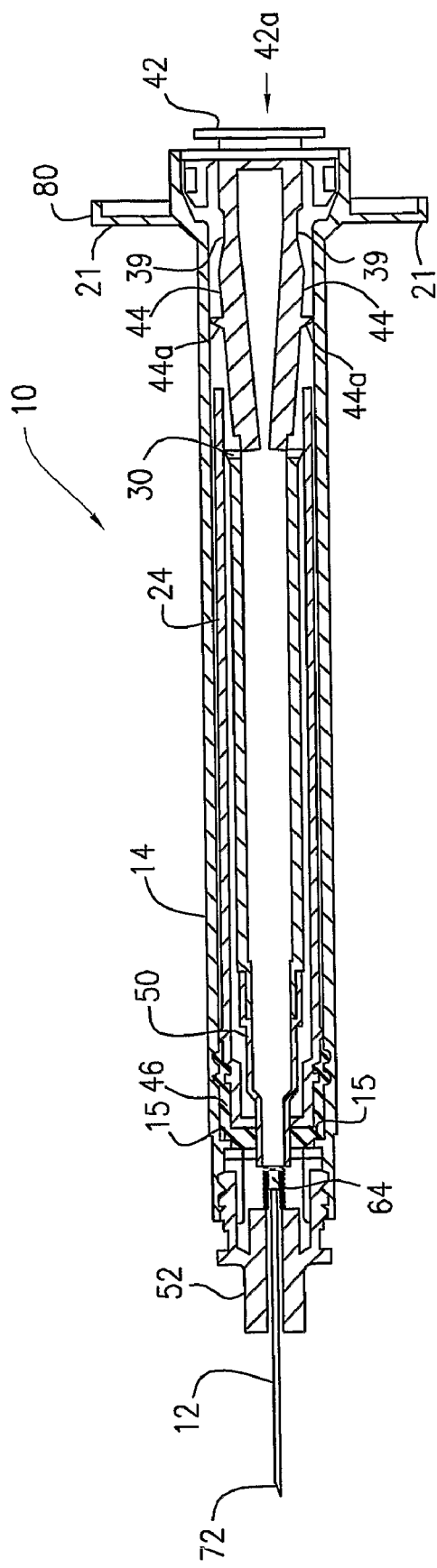
FIG. 19 is a cross-sectional view of the syringe shown in FIG. 1, with the plunger advanced further distally than shown in FIGS. 16-18 and the inner sleeve collapsing within the outer housing of the plunger.
Figure 22:
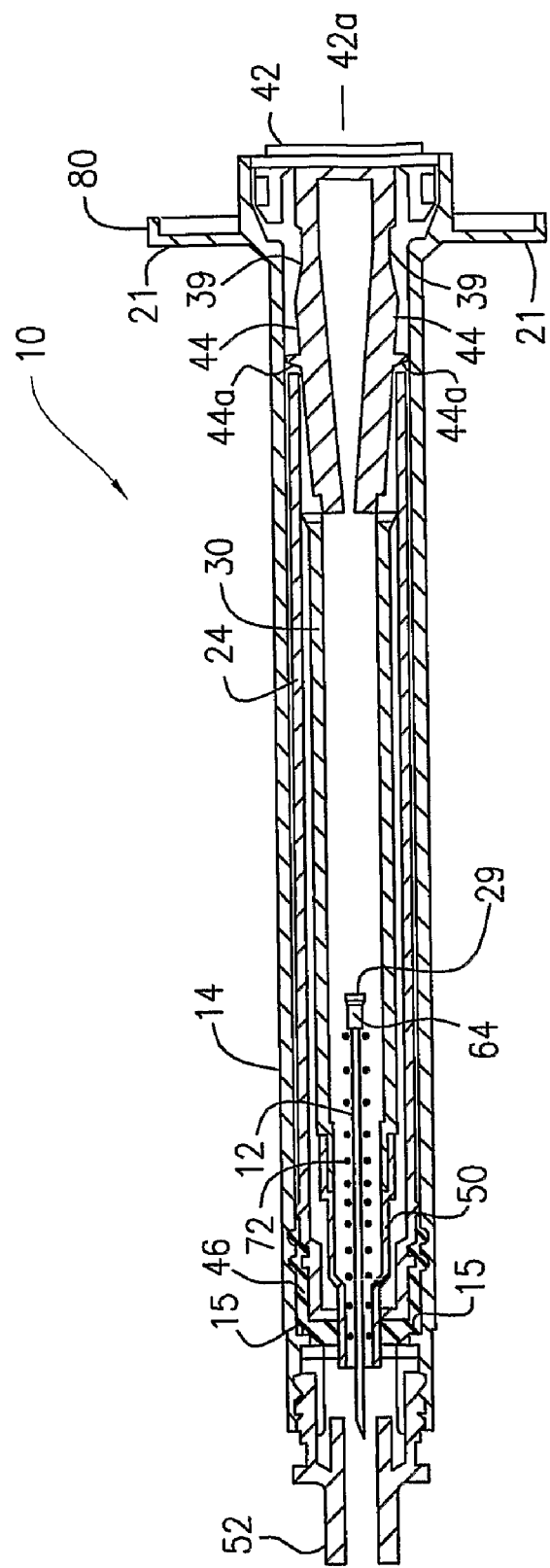
FIG. 22 is an a cross sectional view of the syringe shown in FIG. 1, with the needle retracted into the syringe barrel.

Referring now to FIGS. 19 to 21, as the user continues to apply distally directed force to the thumbpress 42, the stopper 46 compresses as the gap region 53 decreases still further in size, permitting the outer housing 24 and inner sleeve 30 to distally advance further into barrel 14. The compression of the stopper 46 by the decrease in size of gap region 53 permit further distal advancement of the outer housing 30 and inner sleeve 24 cause distal facing incline 47a to engage shoulder 19, causing the fingers 44 to deflect inwardly towards cavity 34. Shoulder 19 thus acts as an activation surface for the fingers 44. Deflection of the fingers 44 allows the inner sleeve 30 to decouple from outer housing 24 and move distally with respect to outer housing 24. The stopper 46 is compressed to an axial length $L_{20}$, which is less than length $L_{17}$ shown in FIG. 17. The fingers 44 act as a decoupling element in cooperation with the shoulder 19. The projection 49 of the stopper is pressed into the axial stem 64. The compression of the stopper 46 ensures that the complete dose of medication is delivered and that there is no dead volume in the syringe barrel Referring now to FIGS. 22 to 24, as the inner sleeve 30 continues to move distally forward with respect to outer housing 24, the cutter 50 on the end of inner sleeve 30 cuts through the webbing 29 on the distal end of outer housing 24, the distal face 46a of stopper 46 to expose cavity 34 in sleeve 30, and flange 62 initiating the retraction of the needle into the cavity 34 of the inner sleeve 30. The bias of the spring 70 urges sufficient movement of the stem 64 having needle 12 mounted thereon into the cavity 34. Thus the needle 12, including its sharp distal point 72 is completely retracted within the inner sleeve thereby substantially preventing inadvertent exposure of the sharp distal point. With the withdrawal of needle 12 into cavity 34, syringe 10 is substantially non-functional and cannot be restored to functionality. Additionally, personnel are substantially protected from inadvertent exposure to sharp distal point 72 of the needle.

The fingers 44 of the inner sleeve 30 of the plunger rod 22 are designed so that the plunger 22 is capable of withstanding distal forces of at least about 26 pounds and up to about 55 pounds when the distal edges 45 of fingers 44 engage distal end 40a of windows 40, which prevents the inner sleeve 30 from decoupling from the outer housing 24. This amount of required force prevents premature decoupling of the outer housing 24 and inner sleeve 30. The syringe of the present invention ensures that a full injection dose of medication is delivered before the retracting safety mechanism is activated. The activation of the retraction mechanism is dependent upon the displacement of the plunger rod and application of force to the stopper, rather than the application of force to the stopper alone or displacement of the plunger rod alone. Thus, the inner sleeve 30 will not decouple from the outer housing 24 until the stopper 46 is bottomed out and compressed against the roof 15 of the barrel 14 and compressed a sufficient amount to allow advancement of the plunger rod 22 until activation of the fingers 44 to cause decoupling of the inner sleeve 30 and outer housing 24.

The compression of the stopper 46, particularly the decrease in size of the gap region 53 on the sidewall, dictates the force required to activate the separation of the inner sleeve 30 and outer housing 24 to initiate retraction. As discussed above, when the stopper 46 is bottomed out against roof 15 of the barrel 14, only a portion of the distal face 46a of the stopper is under pressure, namely the distal contact surface 48a in contact with the roof 15. This permits a greater distal displacement of the plunger 22 for the same amount of force that was applied during delivery of the medication. This is because during delivery of the medication, the distal face 46a of the stopper 46 is under resistance from the fluid pressure of the medicament in the syringe barrel 14. After all medicament has been expelled from the syringe and the entire distal face 46a is no longer under pressure, only the distal contact surface 48a in contact with roof 15 is under pressure. Thus, if the user applies the same amount of force as during medicament delivery, the reduced pressure on the stopper 46 will result in a greater distal displacement of the plunger 22. For example, a comparison of the compression of the stopper 46 due to backpressure during delivery of medicament to the compression of the stopper 46 caused by the barrel roof, there is about a two to three-fold increase in compression distance for the same force applied. Thus, if during delivery of medicament the user applies 15 lbs force to the thumbpress 42, the stopper 46 compresses about the same as when the user applies about 5 lbs force when the stopper 46 is bottomed out on the barrel roof 15 due to the reduction in force from the removal of the medication acting across the entire distal surface 46a of the stopper 46.

The hypodermic needles used in accordance with embodiments of the present invention can be formed from conventional materials such as steel. It will be realized by the skilled artisan that medical grade plastics, composites, ceramics, or like materials can be substituted. The needle can be lubricated with various conventional lubricants such as silicone oils to enhance the effects obtained by applicant's geometry. The hypodermic needles can include needles used for administering medicaments, blood and tissue collection, insulin delivery, catheter products utilizing needles.

Syringe 10 of the invention provides practitioners the ability to deliver high viscosity drugs with a lessened chance of premature retraction of the needle. The components of syringe 10 are compatible with the requirements for high speed manufacture because, as described above, many of the components of syringe 10 do not differ substantially in shape or balance from similar components of conventional syringes.

While the foregoing is directed to embodiments of the present invention, other and further embodiments of the invention may be devised without departing from the basic scope thereof, and the scope thereof is determined by the claims that follow.

What is claimed is:

1. A syringe including a retractable needle comprising:
a barrel having a fluid chamber defining a longitudinal axis and including a proximal end, and a distal end adapted to be attached to a needle;
a plunger rod having a distal end and proximal end, the plunger rod including an inner sleeve slidably engageable with an outer housing, the inner and outer housing being axially moveable with respect to each other upon activation of a decoupling element associated with the plunger rod; and
a compressible stopper mounted on the distal end of the of the plunger rod, the stopper being configured such that when distal force is applied to the plunger rod, the stopper is compressed in the direction of the longitudinal axis in an amount to allow distal movement of the plunger rod along the longitudinal axis a distance sufficient to permit activation of the decoupling element, causing the inner sleeve to decouple from the outer housing and move distally with respect to the outer housing and retraction of the needle within the syringe barrel,
wherein the decoupling element includes one or more flexible fingers formed on the inner sleeve of the plunger rod and the barrel includes an inner surface and a shoulder formed on the inner surface adjacent the proximal end adapted to engage a contact surface on the inner sleeve of the plunger rod, causing the one or more flexible fingers to flex inwardly and permit relative distal movement between the outer housing and inner sleeve.

2. The syringe of claim 1, wherein activation of the decoupling element is dependent upon both compression of the stopper and distal displacement of the plunger rod along the longitudinal axis.

3. The syringe of claim 1, wherein the stopper includes an outer wall portion including a distal rib spaced from a proximal rib defining a gap region in the outer wall, the gap region having a wall thickness that is less than the wall thickness of the proximal rib and the distal rib.

4. The syringe of claim 3, wherein the barrel includes and inner surface and a ceiling located adjacent the distal end on the inner surface to engage the distal rib when the plunger rod is advanced distally within the chamber.

5. The syringe of claim 1, wherein the stopper has an axial length and a diameter, and the axial length of the stopper is at least about 50% of the diameter of the stopper.

6. The syringe of claim 4, wherein the axial length of the stopper is at least equal to the diameter of the stopper.

7. The syringe of claim 1, wherein the inner sleeve and the outer housing are configured such that at least about 26 pounds of distal force can be applied to the plunger rod without decoupling of the inner sleeve and outer housing.

8. The syringe of claim 7, the flexible finger including a distal end and the outer housing includes a wall with a window formed adjacent the proximal end of the plunger rod, the window including a distal end and a proximal end, the finger and the window being sized so that the finger fits within the window and the distal end of the finger engages the distal end of the window to prevent distal axial movement of the inner sleeve with respect to the outer housing when distal pressure is applied to the plunger rod.

9. The syringe of claim 1, wherein the contact surface is a ramped surface.

10. The syringe of claim 1, wherein the inner sleeve further includes a proximal facing edge adapted to engage the outer housing to prevent proximal movement of the inner sleeve relative to the outer housing.

11. A syringe comprising:
a barrel having a fluid chamber, an inside surface, a proximal end, a proximal shoulder located on the inside surface, a distal end adapted to be attached to a needle and a ceiling located on the inside surface and adjacent the distal end; and
a plunger rod having a distal end and a proximal end, the plunger rod adapted to slidingly engage the inside surface of the fluid chamber, the plunger rod including a hollow outer housing defined by a wall and a hollow inner sleeve slidably receivable within the outer housing and defining a cavity, and a stopper located on the distal end of the plunger rod, the stopper including a distal face and an outer wall surface, the outer housing including at least one window extending axially through the wall adjacent the proximal end of the plunger rod, the inner sleeve including at least one flexible finger adapted to be flexed inwardly towards the cavity, the flexible finger including a distal end, a proximal end, a distal facing ramp surface adapted to engage with the shoulder of the barrel and a distal facing edge, the inner sleeve further including a proximal facing stop edge, the finger being sized and shaped to be received within the window, the stopper including a distal rib, a proximal rib and a gap region between the ribs located along the outer wall surface, wherein the configuration of the ramp surface and the stopper is such that axial compression of the stopper permits sufficient axial movement of the plunger rod so that ramp surface engages the shoulder of the barrel, causing inward deflection of the fingers and relative movement of the inner sleeve and outer housing and retraction of the needle.

12. The syringe of claim 11, wherein the at least one window includes a distal end adapted to engage the distal facing edge of the finger to prevent relative distal axial movement of the inner sleeve and outer housing when distal force is applied to the plunger rod.

13. The syringe of claim 12, wherein the finger and distal edge are configured to withstand at least about 26 pounds of distally directed force.

14. The syringe of claim 12, the inner sleeve further including at least one lug located adjacent the proximal end of the plunger rod, the lug sized to fit within a track formed in the wall of the outer housing adjacent the proximal end, the lug including a proximal facing stop edge adapted to engage the housing to proximal movement of the inner sleeve with respect to the outer housing when proximal force is applied to the plunger rod.

15. The syringe of claim 14, wherein the inner sleeve includes a pair of fingers adapted to be deflected inwardly upon contact with the shoulder, the outer housing includes a pair of windows adapted to receive the pair of fingers, the inner sleeve further includes a pair of lugs, and the outer section includes a pair of tracks adapted to receive the lugs.

16. The syringe of claim 15, further comprising a pair of bosses formed on the inner sleeve and a pair of channels that cooperate to align the fingers with the windows and the lugs with the tracks.

17. The syringe of claim 16, wherein the pair of bosses are asymmetrical.

18. The syringe of claim 16, wherein one of the pair of bosses are offset from a centerline of the inner sleeve.

19. The syringe of claim 14, wherein the inner sleeve includes a cutting element mounted on the distal end.

20. The syringe of claim 18, wherein the outer housing includes webbing on the distal end adapted to support the end of the stopper as the stopper is advanced in a distal direction and a needle attached to the distal end of the barrel, the needle attached to a hub including a flange.

21. The syringe of claim 20, wherein inner deflection of the fingers permits distal movement of the inner sleeve within the outer housing, causing the cutting element to cut through the webbing, the stopper and the flange, causing the needle to retract within the barrel.

22. The syringe of claim 18, wherein the stopper includes a distal face, and when the stopper is advanced against the roof of the barrel, only a portion of distal face is contact with the ceiling of the barrel.

* * * * *